(12) United States Patent
Oshio et al.

(10) Patent No.: US 6,684,098 B2
(45) Date of Patent: *Jan. 27, 2004

(54) VERSATILE STEREOTACTIC DEVICE AND METHODS OF USE

(75) Inventors: Koichi Oshio, Tokyo (JP); Lawrence P. Panych, Brookline, MA (US); Charles R. G. Guttmann, Brookline, MA (US)

(73) Assignee: Brigham and Women's Hospital, Inc., Boston, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/868,719

(22) Filed: Jun. 4, 1997

(65) Prior Publication Data

US 2001/0020127 A1 Sep. 6, 2001

Related U.S. Application Data

(63) Continuation-in-part of application No. 08/698,878, filed on Aug. 16, 1996, now Pat. No. 6,080,164.

(51) Int. Cl.⁷ .................................................. A61B 5/00
(52) U.S. Cl. ........................ 600/429; 600/417; 606/130
(58) Field of Search .............................. 600/407, 410, 600/417, 429; 606/130; 128/920, 922

(56) References Cited

U.S. PATENT DOCUMENTS

| | | | |
|---|---|---|---|
| 4,256,112 A | 3/1981 | Kopf et al. ............. 128/303 B |
| 4,431,220 A | 2/1984 | Loughlin | |
| 4,608,977 A | 9/1986 | Brown | |
| 4,617,925 A | 10/1986 | Laitinen ................. 128/303 B |
| 4,618,978 A | 10/1986 | Cosman ..................... 378/164 |
| 4,638,798 A | 1/1987 | Shelden et al. | |
| 4,884,566 A | 12/1989 | Mountz et al. ......... 128/303 B |
| 4,923,459 A | 5/1990 | Nambu | |
| 5,042,462 A | * 8/1991 | Bremer | |
| 5,242,455 A | * 9/1993 | Skeens et al. | |
| 5,263,494 A | 11/1993 | Margelos et al. ........... 128/845 |
| 5,285,787 A | 2/1994 | Machida ................. 128/653.2 |
| 5,330,485 A | 7/1994 | Clayman et al. | |
| 5,383,454 A | 1/1995 | Bucholz ................. 128/653.1 |
| 5,388,059 A | * 2/1995 | DeMenthon ................ 364/559 |
| 5,396,684 A | 3/1995 | Yocom ..................... 24/16 PB |

(List continued on next page.)

FOREIGN PATENT DOCUMENTS

| | | |
|---|---|---|
| GB | 2213066 | 8/1989 |
| JP | 03-267054 | 11/1991 |

OTHER PUBLICATIONS

Tan, K.K. et al., "A frameless stereotactic approach to neurosurgical planning based on retrospective patient–image registration", *J. Neurosurg.*, 79:296–303, Aug. 1993.

(List continued on next page.)

*Primary Examiner*—Ruth S. Smith
(74) *Attorney, Agent, or Firm*—Mintz, Levin, Cohn, Ferris, Glovsky an Popeo, P.C.

(57) ABSTRACT

A stereotactic device for use with an imager such as a magnetic resonance imager is disclosed, which permits an imaging scan to be taken with reference to a personal coordinate system (or PCS) that is independent of a machine coordinate system (or MCS). Methods using the device to obtain imaging scans are described such that the imaging scans are superimposable even if taken at different time periods using the same or a different imager. The device comprises a frame that can be reproducibly positioned on a subject and which is equipped with non-invasive affixing means and localizing means that provide the PCS. The device and methods of the invention are particularly well suited for routine initial or follow-up examinations, pre-surgical planning and post-surgical evaluation. Markers on a stereotactic device can be tracked during an MRI scan to compensate for patient motion during the scan.

32 Claims, 20 Drawing Sheets

U.S. PATENT DOCUMENTS

| | | | | |
|---|---|---|---|---|
| 5,398,684 A | * | 3/1995 | Hardy | |
| 5,408,409 A | * | 4/1995 | Glassman et al. | |
| 5,423,832 A | | 6/1995 | Gildenberg | 606/130 |
| 5,531,227 A | | 7/1996 | Schneider | 128/653.1 |
| 5,588,033 A | | 12/1996 | Yeung | 378/4 |
| 5,588,430 A | | 12/1996 | Bova et al. | 128/653.1 |
| 5,603,318 A | * | 2/1997 | Heilbrun et al. | |
| 5,622,111 A | | 4/1997 | Bachmeir et al. | 101/415.1 |
| 5,622,187 A | * | 4/1997 | Carol | 128/897 |
| 5,676,673 A | | 10/1997 | Ferre et al. | 606/130 |
| 5,681,326 A | | 10/1997 | Lax | 606/130 |
| 5,682,890 A | * | 11/1997 | Kormos et al. | |
| 5,695,501 A | * | 12/1997 | Carol et al. | |
| 5,772,594 A | * | 6/1998 | Barrick | |
| 5,792,147 A | * | 8/1998 | Evans et al. | |
| 5,868,675 A | * | 2/1999 | Henrion et al. | |
| 6,080,164 A | * | 6/2000 | Oshio et al. | 606/130 |
| 6,275,725 B1 | * | 8/2001 | Cosman | 600/426 |

OTHER PUBLICATIONS

John D. Graham et al., "A non–invasive, relocatable stereotactic frame for fractionated radiotherapy and multiple imaging", *Radiotherapy and Oncology*, (1991) 21:60–62.

Lauri V. Laitinen et al., "An Adapter for Computed Tomography–Guided Stereoxtaxis" *Surg. Neurol.*, (1985) 23:559–566.

Koichi Oshio et al., "A Simple Noninvasive Stereotactic Device for Routine MR Head Examinations", *Journal of Computer Assisted Tomography*, 20(4):588–591 (1996).

Hariz, et al., "Reproducibility of Repeated Mountings of Noninvasive CT/MRI Stereoadapter", *Appl. Neurophysiol.*, 49:336–347 (1986.)

* cited by examiner

FIG. 1A
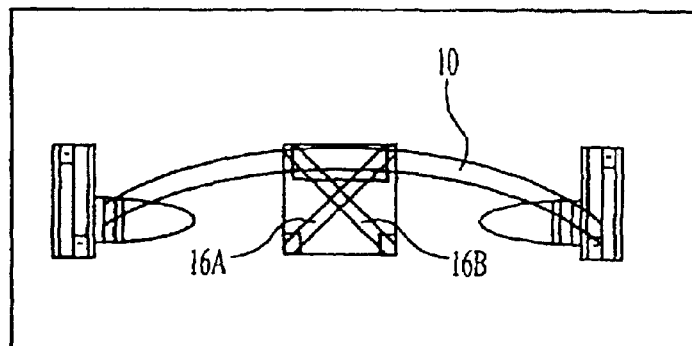
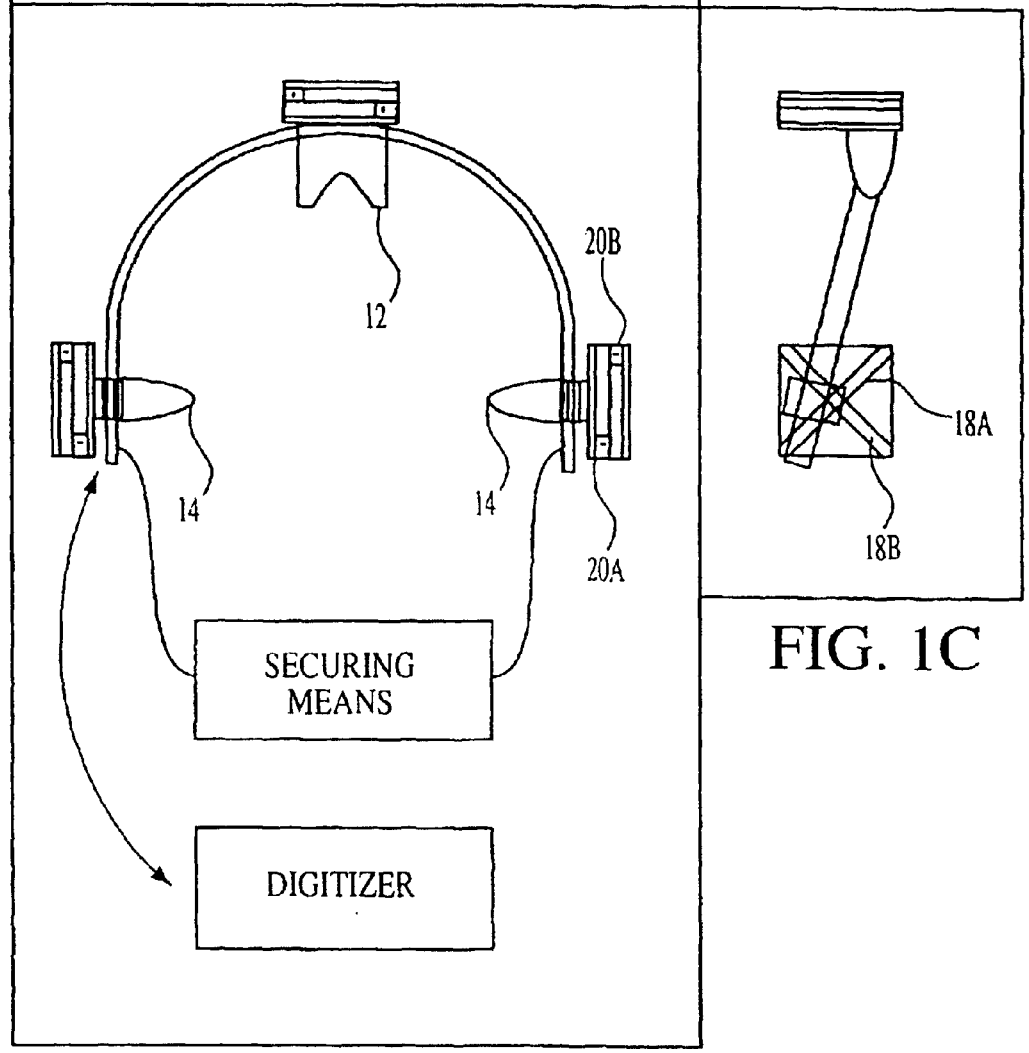
FIG. 1C
FIG. 1B

VERSATILE STEREOTACTIC DEVICE AND METHODS OF USE

CROSS REFERENCE TO RELATED APPLICATION

This is a continuation-in-part of U.S. application Ser. No. 08/698,878 filed on Aug. 16, 1996, now U.S. Pat. No. 6,080,164 issued Jun. 22, 2000, the disclosure of which is incorporated in its entirety by reference herein.

1. FIELD OF THE INVENTION

The invention pertains to a versatile stereotactic device useful in a number of methods, including numerous modes of medical imaging. More particularly, the device and methods of the present invention relate to a non-invasive stereotactic method of reproducibly imaging portions of a patient's body, such as the patient's head and portions of the patient's spine in the proximity of the head. Thus, imaging modalities, including magnetic resonance (MR) imaging, magnetic resonance spectroscopy, computer-aided tomography (CT), positron emission tomography (PET), single photon emission computed tomography (SPECT), electroencephalography (EEG) or magnetoencephalography (MEG) and the like can be used to monitor, diagnose, or detect pathologic conditions and to follow their development, progress, arrest, or remission. The device and methods of the invention are especially applicable to permitting more routine head examinations, pre-surgical planning and providing post-surgical evaluations and prognoses.

2. BACKGROUND OF THE INVENTION

In head examinations involving magnetic resonance imaging, computer-aided tomography and other such techniques, it is desirable to have a well-defined, reproducible coordinate system to record and/or compare the locations and sizes of lesions, tumors and other structures of interest. Though there are a number of known devices and techniques for potential application to these types of examinations, these known devices and techniques are generally not suitable for "routine" office examinations, in which factors such as ease of use, speed of use, comfort, cost, accuracy and reproducibility are of major consideration. Indeed, existing devices are often heavy, unwieldy, cumbersome and require that the devices be affixed to the subject using pins, screws, bolts, brackets, staples and the like.

Several methods have been proposed to find the relative position of a scan "slice" by using anatomical landmarks. In these methods, the size and position of predetermined anatomical structures, such as the lateral end of the internal auditory canal, are used as reference points to help locate and compare lesions and other features of interest. See, e.g., Tan, K. K. et al., in *J. Neurosurg.* (1993) 79:296–303. A problem with this technique, however, is that the image resolution in the scan slice direction (i.e., the z-direction) is poor compared with the resolution in the scan in-plane (x-y direction). Because of this poor resolution, it is difficult to make precise positional determinations. Moreover, these methods also require a degree of anatomical knowledge which may strain the capabilities of the average MR technologist.

As an alternative, the art has developed devices, such as frames and "halos," to facilitate positioning for stereotactic surgery. These devices are rigidly affixed to the patient being imaged and to an imager platform and provide reference points or lines to facilitate the determination of the orientation of the patient's head. See, e.g., U.S. Pat. No. 4,341,220, which discloses a stereotactic surgical frame with fiducial plates that surround the patient's head in the fashion of a boxer's headgear and which provides several non-collinear fiducial points in cross-sectional scans. Most stereotactic frames are fixed to the patient's skull directly, usually by bolts or screws, as noted previously. Clearly such methods are not suitable for "routine" office examinations.

So-called non-invasive, stereotactic devices have also been described. The Gill-Thomas stereotactic frame, which is based on the Brown-Roberts-Wells neurosurgical frame, was designed to be used for a series of stereotactic radiotherapeutic operations. See, Graham et al., in *Radiotherapy and Oncology*, (1991) 21:60–62. This device requires that it be affixed to the patient by a block, tailored for individual patients.

Another device, designed by Laitinen et al., is fixed to the patient by means of a nasion support and two ear plugs. See, e.g., Laitinen et al., in *Surg. Neurol.* (1985) 23:559–566 and U.S. Pat. No. 4,617,925. However, this device is then affixed to the imaging couch or table. Hence, this device is able to permit reproducible scans only by relying on the fixed position of the patient against the couch or table with respect to the machine coordinate system. Again, affixing the patient to the machine may makes the patient uncomfortable during the scan. See, also, U.S. Pat. No. 5,330,485, disclosing a cerebral instrument guide frame that rests on the bridge of the nose (i.e., about the nasion) and which contains plugs for insertion into the external ear canals.

Stereotactic devices are typically fashioned from precision aluminum alloy and are very expensive for all except non-routine use. Moreover, it is usually cumbersome and time consuming to affix these devices to the patient, adding to their unsuitability for routine examinations.

The state of the art suggests that stereotactic devices be equipped with radiographic markers that are visible in scans of a patient's head. For example, U.S. Pat. No. 4,923,459 discloses a stereotactic frame that also includes radio-opaque rods arranged in the configuration of the letter "N" to facilitate localization of a surgical target. U.S. Pat. No. 4,608,977 discloses a helmet-like, stereotactic frame that includes such N-shaped "localizing" rod to facilitate the determination of the location of a CT scan cross-section. Likewise, U.S. Pat. No. 4,638,798 discloses a halo-like stereotactic frame that has a ring with a plurality of pins of differing lengths extending therefrom. The relative location of a scan can be determined from the relative location of the ends of the pins.

Though such devices can be used to determine the location of a head in x-y space, and to determine the relative location of each imaging "slice," they do not permit the position of a head to be fully determined, e.g., as where the head is tilted in the imaging plane.

In addition to the limitations described above, the prior techniques are not generally suitable for direct alignment of images obtained from different imaging modalities. That is, to permit the direct comparison of images obtained from different imaging modalities, say MR and CT, the patient must be re-aligned precisely with respect to the two machine coordinate systems. Alternatively, a correction can be made using image processing techniques after a second or subsequent scan has been taken. However, image processing has the drawback in that the resolution of the processed image is dependent on the quality of the scan data set. It would be desirable to alter a scan in real time such that scans from different modalities can be compared directly without the need for image processing.

In each of the known devices and methods, the anatomical coordinates of the patient are fixed in relation to a reference coordinate system, that is the machine's coordinate system. Thereafter, the machine's coordinate system is used as the reference coordinate system for each subsequent scan. Because of the difficulty in reproducing the machine coordinate system or because different machines are invariably associated with different, incompatible machine coordinate systems, it has not before been possible to relate directly scans from different imaging modalities. Moreover, it is not always possible to align directly scans from the same imaging modality (e.g., MR imagers) when comparing images obtained from machines made by different manufacturers.

It would thus be desirable to have a device and method whereby the reference coordinate system is independent of the machine or imaging modality. It would be desirable, moreover, to use a reference coordinate system "personal" to the patient as the reference coordinate system and, where possible, have the machine's coordinate system fixed or adjusted relative to that of the patient to provide for scans that are reproducible, compatible and superimposable in the same or different imaging modalities. A system that enables the taking of imaging scans under such a patient reference or "personal" coordinate system would be of great utility and would be deemed a significant advancement in the art.

In view of the foregoing, it is an object of the invention to provide improved devices and methods of non-invasive, repetitive, radiographic examination of a subject, particularly of the subject's head.

A further object of the invention is to provide such devices and methods that are readily amenable for use in "routine" examinations, as well as for surgical planning and follow-up.

A still further object of the invention seeks to provide improved devices and methods of stereotaxis (both invasive and non-invasive), which are low-cost, easy to use, comfortable and which provide accurate and reproducible results.

Yet another object of the invention relates to improving methods and apparatuses that can determine fully the position of a head and a scan plane, including when the head is tilted in the scan plane.

Other objects of the invention include providing a way or means for comparing directly scans taken by the same or different imaging modalities and providing a method for the reproducible placement of external markers, e.g., electrodes, on a patient.

3. SUMMARY OF THE INVENTION

The invention thus provides devices and methods for the non-invasive, imaging or radiographic examination of a subject. By "imaging" is meant any scanning or spectroscopic technique that provides information that can be recorded on a tangible medium (e.g., photographic film, slides and the like) or electronically for storage, later retrieval, or manipulation. Moreover, the scanning or spectroscopic technique may also give rise to an image that is viewable, e.g., on a screen or monitor. The immediate objective, of course, is to provide information regarding, or an image of, the internal organs or tissues of a subject. Such scanning or spectroscopic technique or imager can use a wide variety of electromagnetic radiation (or for that matter any suitable source of energy) to probe or excite internal atoms, ions, molecules, structures, cells, tissues, or organs, including but not limited to radio waves, infrared, ultrasound, ultraviolet, X-rays, electron beam, alpha-, beta-, or gamma-rays or particle emissions.

Accordingly, the invention provides a stereotactic device that is intended for use with an imager and generally comprises a frame equipped with localizing means and affixing means. The localizing means comprises one or more localizing arrays that provide one or more imager detectable signals, while the affixing means comprises non-invasive fittings for placement about the periphery of the subject and which permit the reproducible positioning of the frame on the subject. From the signals is derived a personal coordinate system that serves as a reference coordinate system for imaging scans taken of a subject on which the frame is positioned. This personal coordinate system is independent of any machine coordinate system. (Contrast the device of Laitinen et al., for example, which must be attached to the imaging table or couch to "fix" the device's (and consequently the patient's) coordinate system to that of the machine coordinate system.) In a specific embodiment of the invention, the localizing means comprises localizing arrays or individual reference elements. Alternatively, the localizing array may be made up of one or more reference elements. The resulting three-dimensional reference coordinate system is specific or "personal" to the subject and is independent of the machine coordinate system.

The device, as described further below, may be reproducibly positioned to the subject without the need for an invasive affixing means, such as staples, pins and/or bolts (i.e., the device of the invention is "non-invasive"; non-invasive can also mean the absence of a surgical intervention or of a breach of a subject's body).

The invention also relates to method of obtaining imaging scans of a subject which includes providing a non-invasive stereotactic device that is positioned reproducibly on a subject and which device establishes a personal coordinate system (PCS) associated with the subject. Again, the PCS is independent of a machine coordinate system (MCS) associated with an imager.

Subsequently, using an imager having an MCS, an imaging scan of the subject is taken (including the stereotactic device) to establish the PCS of the subject. The MCS of the imager is then manipulated to bring the MCS in substantial alignment with the PCS of the subject. One or more additional imaging scans of the subject are taken next, with the MCS of the imager substantially aligned with the PCS of the subject, to provide a first set of imaging scans.

In yet another aspect of the invention, a method of obtaining imaging scans of a subject taken over different time periods is disclosed. The method comprises taking at a first time period, using an imager, a baseline imaging scan that is relatable to a personal coordinate system (PCS) and a first machine coordinate system (MCS). The PCS, by definition, can be regenerated from the subject in a substantially reproducible manner independent of the imager's (or machine's) coordinate system. At a different time period, using a second imager, at least one follow-up imaging scan is taken, which scan is relatable to the PCS and a second MCS. The second MCS is then manipulated, such that the relationship between the second MCS and the PCS is substantially the same as the relationship between the first MCS and the PCS. At least one additional follow-up imaging scan is then taken, which imaging scan can be superimposed on the baseline imaging scan. The second imager may be the same as or different from the initial "baseline"

imager. It should be understood that follow-up scans can be taken over a wide range of time periods, from very short, essentially back-to-back scans to much longer time periods of days, to weeks, to years.

A further method of the invention relates to yet another method of obtaining imaging scans of a subject. The method comprises providing a subject with a non-invasive stereotactic device that is positioned reproducibly on a subject. The stereotactic device, when positioned on the subject, establishes a personal coordinate system (PCS) associated with the subject which, as always, is independent of a machine coordinate system (MSC) associated with an imager. The method continues with a step of taking, using a first imager having a first MCS, at least one imaging scan of the subject including the stereotactic device to establish the PCS of the subject and to relate the PCS of the subject to the first MCS of the first imager. The next step involves taking, using a second imager having a second MCS, at least one imaging scan of the subject including the stereotactic device to reestablish the PCS of the subject and to relate the PCS of the subject to the second MCS of the second imager. The second MCS is then manipulated, such that the PCS is related to the second MCS in substantially the same way as the PCS is related to the first MCS. The method may further comprise taking one or more additional imaging scans of the subject with the second MCS of the second imager so manipulated.

In this manner, the invention provides a device and methods by which temporally different imaging scans from the same or different imaging modalities can be compared directly.

The device and methods of the invention thereby satisfy a long felt need in the art by providing a way to define or obtain a personal coordinate system that is independent of the machine coordinate system, the time at which the imaging scans are taken, the operator of the imager, the brand name of the imager, the model of the imager, or even the modality of the imager.

An exemplary stereotactic device and method of the present invention can thereby facilitate routine examinations of a patient or subject. In particular, the subject's head can be easily and repeatedly examined with the confidence that imaging scans taken at different time periods can be superimposed or compared directly. In some cases, portions of the patient's spine can also be viewed routinely, e.g., during regular, pre- and post-surgical planning examinations. The imaging modalities that can be used to advantage (or used with each other in any combination, except that the imaging modality that has a "fixed" —not adjustable—machine coordinate system should preferably be used to obtain the first, baseline, or initial set of imaging scans) include MR, CT, PET, SPECT, MEG, and other such imaging/radiologic scanning or spectroscopic techniques.

The invention relates to a method of using a radiographic device by establishing a personal coordinate system referenced to the body of a living organism, establishing a linkage between the personal coordinate system and a machine coordinate system of the radiographic device, and translating data captured in the machine coordinate system to data referenced in the personal coordinate system. A transformation matrix links the personal coordinate system and the machine coordinate system. The transformation matrix can be a rotation matrix or a matrix which combines rotation and translation. Alternatively, a rotation matrix can be combined with a translation vector to link the personal coordinate system and the machine coordinate system. The transformation matrix can be determined using data from a single slice of radiographic data or from data from two or more slices.

The invention is also directed to a system for reproducibly capturing radiographic images, including a radiographic scanner, a stereotactic device, and a computer controlling the radiographic scanner and receiving output information from the scanner to detect the location and orientation of the stereotactic device. The computer is configured to store data referenced to a coordinate system defined with reference to the location and orientation of the stereotactic device. The computer is configured to translate position information controlling the radiographic scanner into position information referenced to the coordinate system defined with reference to the location and orientation of the stereotactic device.

The invention is also directed to a system for reproducibly capturing radiographic images, including a network, a radiographic scanner, a stereotactic device, and a computer, connected to the network, controlling the radiographic scanner and receiving output information from the scanner to detect location and orientation of the stereotactic device. The network is connected to one or more of (a) a host computer, (b) a workstation and (c) a gateway.

The invention is also directed to a computer program product including a memory, and a computer program stored on the memory, the computer program containing instructions for a. establishing a personal coordinate system referenced to the body of a living organism, and b. establishing a linkage between the personal coordinate system and a machine coordinate system of a radiographic device. The computer program further contains instructions for translating data captured in the machine coordinate system to data referenced in the personal coordinate system.

The invention is also directed to a computer program product including a memory, and a computer program stored on the memory, the computer program containing instructions for determining location and orientation of a stereotactic device from either a single slice of radiographic data or from two or more slices.

The invention is also directed to a method of using a radiographic device, including fitting a stereotactic device to the body of a living organism so that the fitting is reproducible, and using the stereotactic device to determine the location of one or more data points from one or more radiographic scans of the body.

These and other aspects of the invention are evident from the discussion above and from the more detailed descriptions that follow of the preferred embodiments of the invention.

4. BRIEF DESCRIPTION OF THE DRAWINGS

A better understanding of the invention may be attained by reference to the drawings, provided herein, in which:

FIG. 1A depicts a front view of one embodiment of a non-invasive, stereotactic device according to the invention;

FIG. 1B depicts a top view of one embodiment of a non-invasive, stereotactic device according to the invention;

FIG. 1C depicts a side view of one embodiment of a non-invasive, stereotactic device according to the invention;

FIG. 4A depicts a scan of a volunteer's head on which is placed the device of FIGS. 1A, 1B and 1C, while

FIG. 6A depicts a scan of volunteer's head on which is placed the device of FIGS. 1A, 1B and 1C while

5. DETAILED DESCRIPTION OF THE INVENTION

Figure 2:
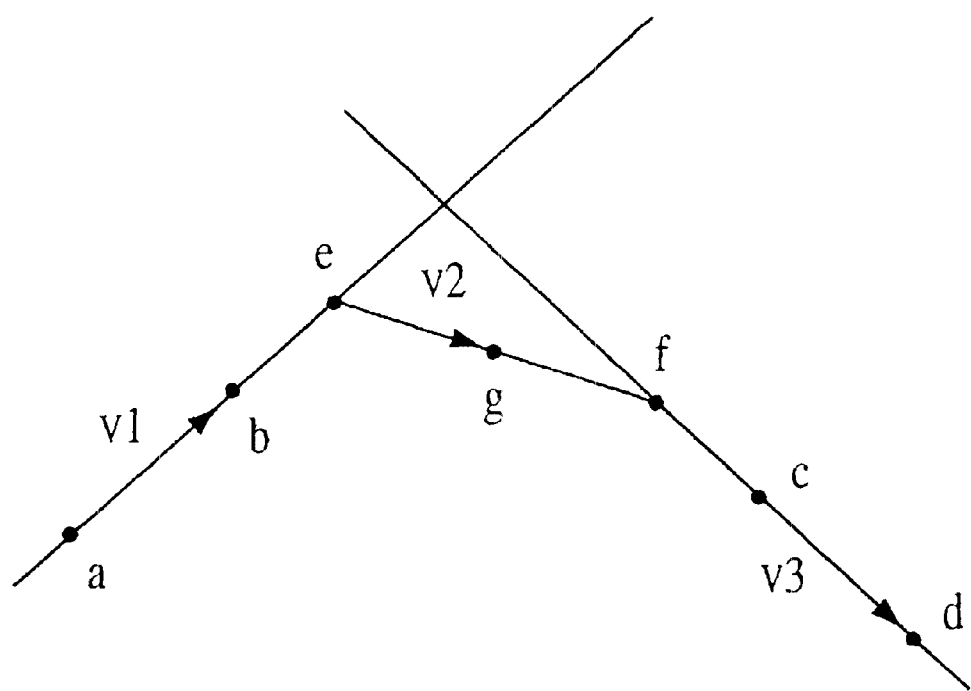
FIG. 2 illustrates a technique for determining the exact position of reference elements based on a pattern of "dots" formed in a scan by the device of FIGS. 1A, 1B and 1C.

The illustrative device and method permit the alignment of routine scans to a pre-defined personal coordinate system. Once this alignment is performed, the location, orientation and size of, e.g., lesions can be reproducibly and precisely determined. It thus becomes possible to compare locations and size from different examinations at different times and sites using different machines for a given modality. It is further possible using the stereotactic device of the invention to provide for imaging scans that can be aligned directly and compared across different imaging modalities.

To accomplish further the objectives of the present invention, the following detailed description is provided which is directed to the lightweight frame, including non-invasive affixing means, localizing means and reference elements for defining a personal coordinate system and a computational procedure for the manipulation and/or alignment of coordinate systems to permit imaging scans to be taken at different time periods which are superimposable or directly comparable.

5.1. Lightweight Frame

In a particular embodiment of the invention, a stereotactic device comprises a lightweight frame having affixing means comprising non-invasive fittings for placement about the periphery of the subject and which permit the reproducible positioning of the frame on the subject. The non-invasive fittings may include, for example, ear fittings and a nose fitting. The frame is adapted to fit partially or completely around the human head. When present, the nose fitting may rest on the nasion or on or about the bridge of the nose. Also when included, the ear fittings (usually a pair) may be inserted into the ears or allowed to rest over them (e.g., in substantially the same manner as eye glass frames rest on the bridge of the wearer's nose and over the wearer's ears).

Moreover, localizing means, described further below, are preferably conveniently positioned in the proximity of the nose and ear fittings (e.g., one by the nasion and one for each ear fittings for a total of three localizing means). In this way, a cross-sectional imaging scan using an MR, CT, PET, SPECT, MEG, and/or such other imager can cut across all three localizing arrays of the localizing means in a single slice.

The frame may be equipped with additional, optional features, such as a securing means that facilitates the further holding or securing of the frame to the subject, especially the subject's head. Such securing means include, but are not limited to, elastic or inelastic components, e.g., fabrics, VELCRO bands and spring assemblies. Preferably, such optional securing components are integrated with the aforementioned ear fittings. Alternatively, these components may be integral with or detachable from the frame.

FIGS. 1A, 1B and 1C depict front, top and side views of an illustrative stereotactic device according to one embodiment of the invention. The stereotactic device comprises a curved frame 10 which is worn by the subject in a manner somewhat similar to eyeglass frames. The stereotactic device further comprises affixing means, including a nose fitting 12 fixed to the midpoint of the frame and a pair of ear fittings 14. In some embodiments, the ear fittings are adjustable, slidably mounted along the frame to accommodate the configuration of the subject's head. The nose fitting is preferably placed on the nasion, and the ear fittings are preferably placed in, on, or over the ears, more preferably in the outermost portion of the external auditory canals.

Referring again to FIG. 1A, the frame 10 can be of variable length, preferably, a length of approximately 15 inches or so, and is formed into a shape providing for comfortable use on a typical human adult. Such a shape may be, e.g., a slight curve, a half circle, a "U," or the like. Different sizes can also be made to accommodate smaller-sized heads, such as an adolescent's or child's head.

Preferably, the materials used for making the frame are low-cost, non-magnetic and transparent to the imaging system. Moreover, the materials should be durable and preferably amenable to repeated sterilization (especially when implementing non-disposable frames). Preferred materials for the frames include relatively rigid thermoplastic materials, including most synthetic polymers but most preferably plexiglass.

5.2. Localizing Means

In this aspect of the device, the frame is equipped with localizing means comprising one or more, preferably at least three, of what are referred to herein as localizing arrays. Each array provides one or more imager detectable signals from which the personal coordinate system of the subject is derived. With the personal coordinate system serving as the reference coordinate system for the initial, baseline imaging scans and each subsequent follow-up imaging scans, the stereotactic examination of the subject is facilitated.

In a particular embodiment of the invention, the localizing array is made up of one or more reference elements, preferably including a pair of reference elements. A suitable reference element may comprise an elongate component, e.g., a cylindrical rod or tube. Other localizing means and corresponding localizing arrays would be apparent to one of ordinary skill on appreciation of the disclosure provided herein. For example, a localizing array may comprise a supporting means, such as a cylindrical guide directed toward the body of the subject, into which a digitizing "pen" can be inserted. The digitizer can, in turn, emit signals that can be observed and/or recorded on an imaging scan. Also, depending on the number of localizing arrays, which are provided with a frame, the reference elements can include spherically shaped, egg-shaped, or irregularly shaped "opaque" (more, below) materials to create points in space.

The preferred elongated pair of reference elements can have a number of configurations but are preferably arranged in a spaced-apart "X" configuration. In one embodiment of the invention, the elongate components of each pair form an "X" but do not intersect. Rather, the elongate components (e.g., rods or tubes) are staggered from one another so as to be spaced apart. Thus, e.g., the reference elements of an array, positioned in the proximity of, or at, the nasion, inscribe an "X" configuration when viewed initially from the front of the head and form spaced apart, substantially parallel lines when viewed from the top of the head at approximately a ninety degree angle from the initial view. Generally, the reference elements can be spaced apart by any practical distance, but preferably range from about 0.1 to about 1 inch, more preferably, about 0.2 to about 0.5 inch.

The reference elements are constructed or filled with materials that produce distinctive features in an imaging scan, such as a radiographic scan using an MR imager or CT scanner. For example, the reference elements can be filled with doped water, which is relatively "opaque" (i.e., give rise to detectable signals in the course of the imaging scan) to MR, or they can be constructed of a material that is itself opaque to MR (e.g., stainless steel). When such a stereotactic device is worn on, e.g., the head of, a patient being scanned, the reference elements appear as "dots" (in the case of cylindrical, rod-like, or spherical components) or other distinctive features (in the case of non-cylindrical or irregularly shaped components) in the resulting scan.

Referring again to FIGS. 1A, 1B and 1C a localizing means is shown comprising three localizing arrays, each array in turn comprising paired reference elements 16A/16B, 18A/18B and 20A/20B. The three localizing arrays are each mounted on three ear and nose fittings, as shown. Each pair of reference elements is arranged in the form of an "X," when viewed from the front (tubes 16A/16B) or side (tubes 18A/18B and 20A/20B) and is constructed from, or preferably filled with, a radiographically detectable substance, such as doped water.

Figure 4A:
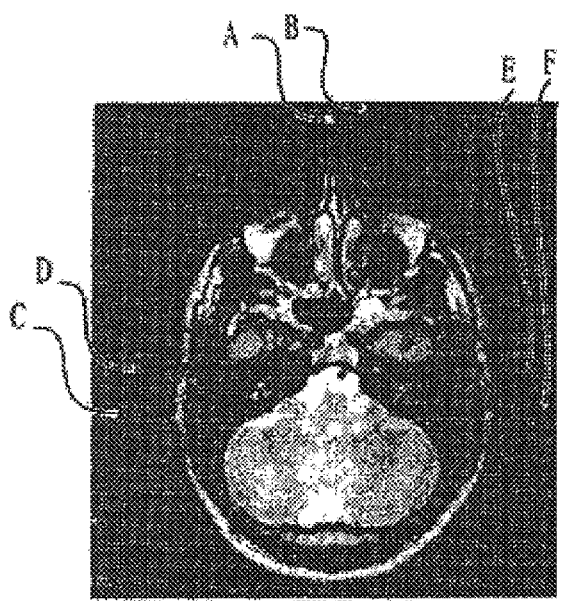
Figure 4B:
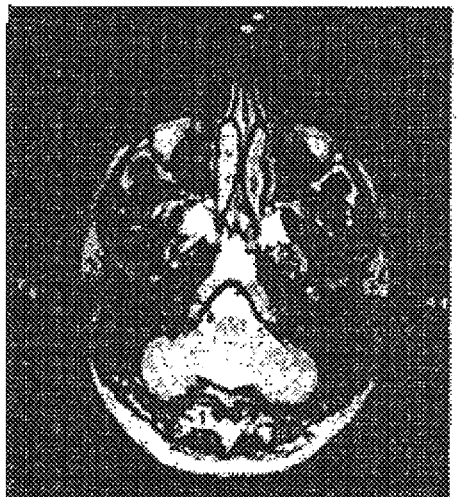
FIG. 4B depicts a modified scan rotated and translated according to a methodology of the invention.

In cross-sectional, radiological scans, such as MR images, the paired reference element tubes appear as two dots at each fitting or location, six dots in toto. Those dots are shown in FIGS. 4A and 4B, where dots a and b correspond to the cross-sectional image of the paired reference elements 16A/16B, respectively; dots c and d correspond to the image of the paired reference elements 20A/20B; and dots e and f correspond to the image of the paired reference elements 18A/18B.

As stated above, the reference elements may be made of a variety of materials or combinations thereof, including plexiglass or other non-magnetic, radio-transparent material that is filled with a radio-opaque substance. Alternatively, these elements may be formed from a radio-opaque substance, such as steel or other metal. The reference elements can be circular in cross-section (e.g., with a radius of approximately 0.05 to approximately 0.4 inch, preferably about 0.2 inch, more preferably about 0.1 inch) or of any other cross-sectional shape readily discernible on a scan. Where the reference elements are in the form of cylindrical tubes, they are generally from about one to about five inches in length, preferably about two inches in length.

In one embodiment of the invention, in which the reference elements are paired, the members of each pair are generally spaced apart from one another. This spacing may be about 0.1 to about 0.5 inch but is most preferably about 0.2 inch.

The reference elements are mounted on plexiglass or other non-magnetic, radio-transparent support of any size suitable for providing a supporting surface for the tubes without making the stereotactic device unwieldy. For example, squares of approximately one-by-one inch to five-by-five inches, preferably about two-by-two inches, more preferably about 1.4×1.4 inches, are suitable for use as the support for the reference elements. Hence, in a particular embodiment of the invention, the combination of support and the reference elements comprise a localizing array. In another embodiment of the invention, a support may also serve as a guide for a digitizing "pen" that can be manipulated by a physician or technician and which generates detectable signals at locations that can be observed and pinpointed in an imaging scan. In still other embodiments of the invention, supports may be dispensed with and the reference elements are found directly on or in the frame (e.g., the elements may be an integral part of the frame).

As used herein the term "radio-opaque" and "radiographically opaque" refer to materials, such as doped water, which are visible on an MRI scan or on such other radiologic scan. Of course, a generally "opaque" material can be chosen so that detectable signals can be observed in each, or some, of MR, PET, SPECT, CT, MEG, or X-ray, as the case may be, and using which material portions of the stereotactic device (e.g., the reference elements) according to the invention are made. Likewise, the term "radio-transparent" refers to materials, such as plexiglass, plastics and most synthetic polymer materials, which are generally not visible on an MRI scan or on such other radiologic scan (e.g., PET or SPECT), with which portions of the stereotactic device (e.g., the frame) according to the invention is used. Such radio transparent materials can also be used in combination with radio opaque materials, as would be apparent to one of ordinary skill. It should be noted that plexiglass, plastics and most synthetic polymers are visible, and thus opaque, in certain imaging modalities, such as CT or X-ray.

5.3. Imaging Procedure

To analyze a scan that includes an image of the reference element tubes, a reference point is first defined; most suitably, the cross-point of each pair of reference element tubes in the above-described "X" configuration can serve as this reference point. Assuming the image is in the in-scan plane, e.g. as in FIGS. 4A and 4B, the x and y coordinates of the reference point can be found as the mid-point between two dots on the image. The z coordinate, or the through-plane position, is determined from the distance of the two "dots" generated by each tube. As a result, the three-dimensional positions of three reference points (one from each pair of tubes) with respect to the MCS are obtained from a single axial image. These reference points, in turn, define the personal coordinate system.

The machine coordinates (i.e., the machine coordinate system) can then be adjusted to rotate and translate the scan to a predetermined plane defined by the personal coordinate system. In this manner, the machine coordinates system can always be made to coincide with reference points that are independent of the machine and which are determined in relation to the specific patient or subject. Hence, a series of imaging scans can be obtained of the same patient at different times, independent of the operator or the specific imaging instrument, all of which are substantially superimposable on one another, including the initial set or baseline set of imaging scans. Also, images from differing imaging modalities can be "merged" by using the stereotactic devices and methods of the invention to provide a composite image comprising superimposed images taken from one or more different imaging modalities.

More particularly, analysis of an imaging scan to determine the position of the reference elements of the aforementioned stereotactic device can be accomplished by the methods of the invention, such as those described in detail, below.

5.3.1. Two-Scan Exact Positioning Method

From two or more imaging slices that cut through both tubes of each of the three localizing arrays, the exact location of the reference point can be calculated mathematically as follows.

Referring again to FIG. 2, points a, b, c and d are where the two planes of the two imaging slices cut through the staggered "X" (thin lines). The x, y and z coordinates in the initial imaging coordinate system can be read from the images. In addition, e and f are points on the tubes where the two tubes are closest to each other, and the reference point, g, can be defined as the mid-point between e and f. The objective is to find the coordinates of g, given coordinates of a, b, c and d.

Two unit vectors, parallel to each of the tubes, $V_1$ and $V_3$, can be defined as:

$$V_1 = \frac{b-a}{|b-a|}$$

$$V_3 = \frac{d-c}{|d-c|}$$

Also, a third vector which is orthogonal to v1 and v3 can be defined as:

$$V_2 = V_1 \times V_3$$

where × denotes the vector (outer or cross) product.

Then line segments a-e-f-d can be expressed as:

$$AV_1 + BV_2 + CV_3$$

where A, B and C are (scalar) distances between a and e, e and f, and f and d, respectively.

Since the vector a–>e+e–>f+f–>d is also equal to a–>d, then $V_4$ can be defined as:

$$V_4 = d - a$$

and $$V_4 = [V_1 V_2 V_3] \begin{bmatrix} A \\ B \\ C \end{bmatrix}$$

Since $V_1$, $V_2$ and $V_3$ are orthogonal, A, B and C can be obtained as:

$$\begin{bmatrix} A \\ B \\ C \end{bmatrix} = [V_1 V_2 V_3]^{-1} V_4 = [V_1 V_2 V_3]^T V_4$$

where "T" is transpose.

The point g is:

$$g = a + AV_1 + \frac{B}{2} V_2$$

For the above-described computational method to work well, the relative position of the two reference element tubes in each localizing array must be defined by some known, non-zero angle. The above steps are simplified by assuming that the two tubes in each localizing array are orthogonal to each other. However, the above-described method also works as long as two tubes have any pre-determined, non-zero angle. In that case, however, the inversion of $[V_1 V_2 V_3]$ becomes necessary, as will be apparent to one skilled in the art.

It is further preferable for the sake of simplicity in calculating the scan position to have the angles between the tubes in each localizing array to be the same. Again, however, this is not critical under the practice of the invention so long as the angles of the tubes in each localizing array are known.

5.3.2. Single-Scan Positioning Method

It is also possible to determine the position of the reference point from a single slice relatively accurately, although mathematically not exact. Assuming the imaging scan is in the x-y plane, the x and y coordinates of the reference point can be found as the mid-point between two dots on the image. The z coordinate, or the through-plane position, can be determined from the distance between the two dots. Since the two tubes are arranged in a staggered "X" configuration, the direction in the z axis can be determined knowing the angle between the elongated components. As a result, the positions of three reference points in all three dimensions are obtained from a single axial image.

Figure 3:
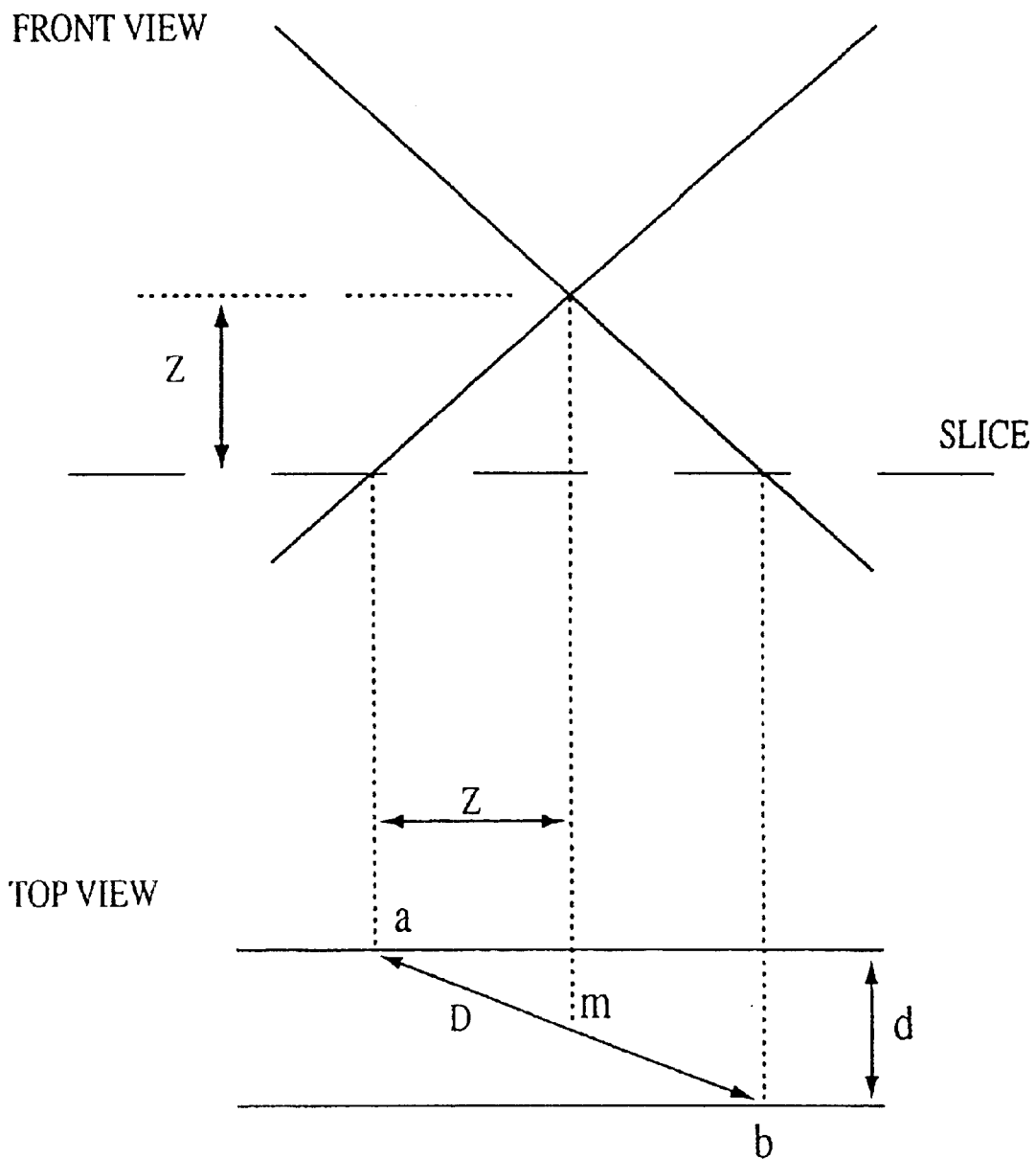
FIG. 3 illustrates another technique for determining the position of reference elements based on a pattern of "dots" formed in a scan by the device of FIGS. 1A, 1B and 1C.

Referring now to FIG. 3, points a and b are where the imaging plane (thin line) cut through the staggered "X" (thick lines). The distance D is defined as the distance between the points a and b on the image and corresponds to the distance between the two tubes that make up the "X" of the localizing array. The x and y coordinates of the reference point, m, can be found on the image as the midpoint between the dots. The z coordinate of the reference point, z, can be calculated as:

$$z = \sqrt{\left(\frac{D}{2}\right)^2 - \left(\frac{d}{2}\right)^2}$$

5.3.3. Computational Method

The detailed calculation method for determining the orientation of a patient's head is as follows:

Let p1, p2 and p3 be vectors representing three reference points in the initial image coordinate system corresponding to a/b, c/d and e/f in FIG. 4A, respectively. These points are calculated as described above. Then, unit vectors representing the new, desired personal coordinate system, x, y, z, can be calculated as:

$x = p3 - p2$ $z = x \times (p1 - p2)$ $y = x \times z$ where × denotes the vector product operation. A rotation matrix that rotates these into xyz axes is obtained as:

$$R = \begin{bmatrix} x^T \\ y^T \\ z^T \end{bmatrix}$$

where "T" is transpose and the translation vector t, is $$t = -R \frac{p2 + p3}{2}$$

Figure 5:
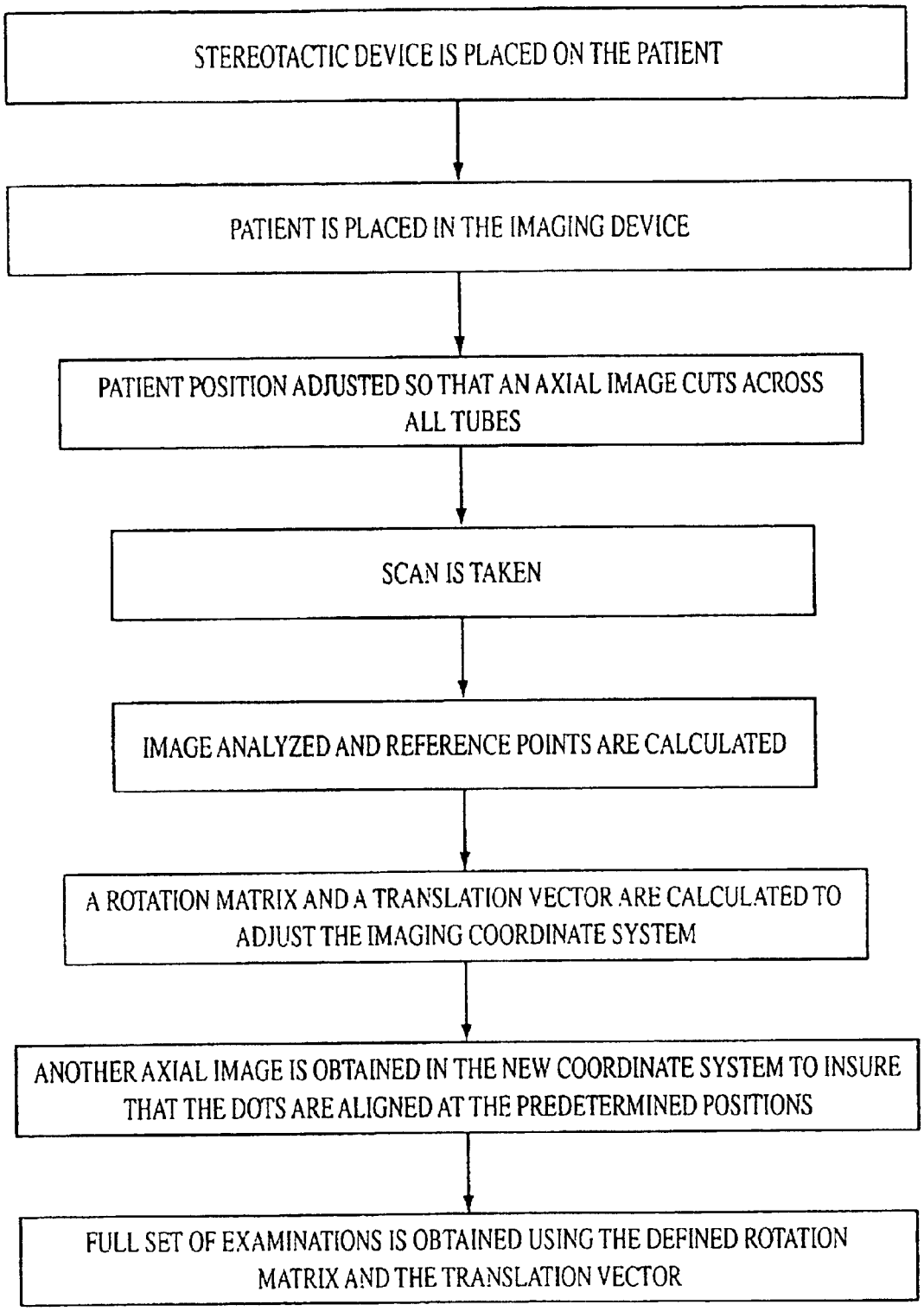
FIG. 5 is a flow chart showing a diagnostic procedure according to the invention for determining the orientation of a patient's head.

A general diagnostic method according to the invention is outlined in FIG. 5, including determining a standard reference coordinate system that is based on the personal coordinate system. First, a stereotactic device, as described above, is placed on the patient. Next, the patient is placed in the imaging device while wearing the stereotactic device. The patient position is adjusted so that an axial image cuts across all tubes in at least three localizing arrays. A scan is taken subsequently. An exemplary resulting scan is shown in FIG. 4A.

From such a scan, the three patient reference points of the personal coordinate system are calculated as described above. From these points, a rotation matrix and a translation vector are calculated to adjust the initial imaging coordinate system to the personal coordinate system, as defined by the stereotactic device. On the MR imager, these transformations are applied to the gradient fields, receiver frequency and phase to change the machine coordinate system.

Next, another axial imaging scan is obtained in the new standard reference coordinate system and the "dots" are checked to ensure that the "dots" are aligned at the predetermined positions. The scan of FIG. 4A, modified in accord with this method of the invention, is shown in FIG. 4B.

Once a standard reference coordinate system is determined by the foregoing steps, then a full set of examinations is obtained using the defined rotation matrix and the translation vector. The entire image alignment process can be performed in a minimal time as compared to previously known scanning techniques in which an attempt is made to adjust or fix the patient coordinate system each time relative to the coordinate system of the imager.

5.4. Additional Supporting Disclosure

A still further aspect of the invention provides a stereotactic device for non-invasive stereotactic examination, particularly of the head of a subject, comprising a frame that is reproducibly positioned on the subject. The frame may have any number of localizing means comprising radio-opaque reference elements to provide for a multi-dimensional reference coordinate system. In a preferred embodiment, six reference elements are included, which are arranged in pairs to provide three localizing arrays.

The frame of the stereotactic device is preferably made of a non-radiographic material, preferably plexiglass. Other suitable radio-transparent materials include, but are not limited to plastics, synthetic polymers, or other carbon-based materials of some structural rigidity, such as poster board, cardboard, or even graphite.

In a particular embodiment, the frame provides a three-dimensional framework for the at least four reference elements to provide a three-dimensional personal coordinate system. In such an embodiment, the localizing means comprises four or more localizing arrays each comprising a reference element. Each reference element, in turn, defines a point in space, three of which points define a unique plane and the fourth point lying outside the unique plane.

In yet another embodiment three reference elements can be designed into the device to provide inherently the fourth reference element necessary to define a three-dimensional space (e.g., as described earlier, confining two of the three reference elements to a pre-determined plane).

The reference elements are positioned on the frame at predetermined positions to provide the three dimensional coordinate system. As described above, the reference elements can be paired in an orthogonal arrangement and be constructed or filled with materials that produce "dots" or other distinctive features in an imaging scan plane. These elements make up the localizing means that provides a reproducible localization of the multi-dimensional personal coordinate system. Thus, the reference elements may include markings such as small paint spots, indentations, slots, grooves, and the like, in or on the frame whose positions can be entered into or recorded in a scan via, e.g., an MRI-compatible digitizer.

Hence, in a preferred embodiment of the invention a stereotactic device for use with an imager comprises a frame equipped with localizing means and affixing means. The localizing means comprises three or more localizing arrays each equipped with two or more reference elements that together provide six or more imager detectable signals. The affixing means comprising three or more non-invasive fittings for placement on the subject's nasion and in or about the subject's ears. The fittings, together, permit the reproducible positioning of the frame on the subject and the reference elements each provide an imager detectable signal. The personal coordinate system is then derived from these signals, collectively.

The reference elements preferably comprise elongate components. For example, two elongate components are arranged in an "X" configuration and are related to one another by a predetermined angle, e.g., about 90 degrees. Further, the reference elements comprise radiographically opaque or semi-opaque material, including steel or doped water. The signals obtained from the reference elements are preferably detectable by MR, CT, PET, SPECT, EEG, or MEG. In an alternative embodiment, the imager detectable signals are provided by a digitizer used in conjunction with the one or more localizing arrays.

The preferred device may further comprise a securing means that facilitates the securing of the frame to the subject. Such securing means may include an inelastic or elastic component.

In use, the stereotactic device is reproducibly positioned on the head of a subject. The position of the reference elements with respect to the desired location of the subject is then digitally recorded, e.g., with an MRI-compatible digitizer. The digitized positions of the reference elements provides a reproducible personal coordinate system. Subsequently, the positional rotation and translation necessary to bring the machine coordinate system into alignment with the personal coordinate system can be determined, preferably by a digital processor. After the machine coordinate system is adjusted to align with the personal coordinate system, one or more radiographic scans are taken.

In subsequent scans, the patient again reproducibly dons the stereotactic device and the positions of the reference elements are digitally recorded. The second imager is then adjusted to the personal coordinate system by means of a translation and/or rotation of the second imager's machine coordinate system, as above. The second and subsequent scans are then taken, again in the patient coordinate system. By scanning each time in the patient coordinate reference system, all scans can be directly compared.

Figure 9:
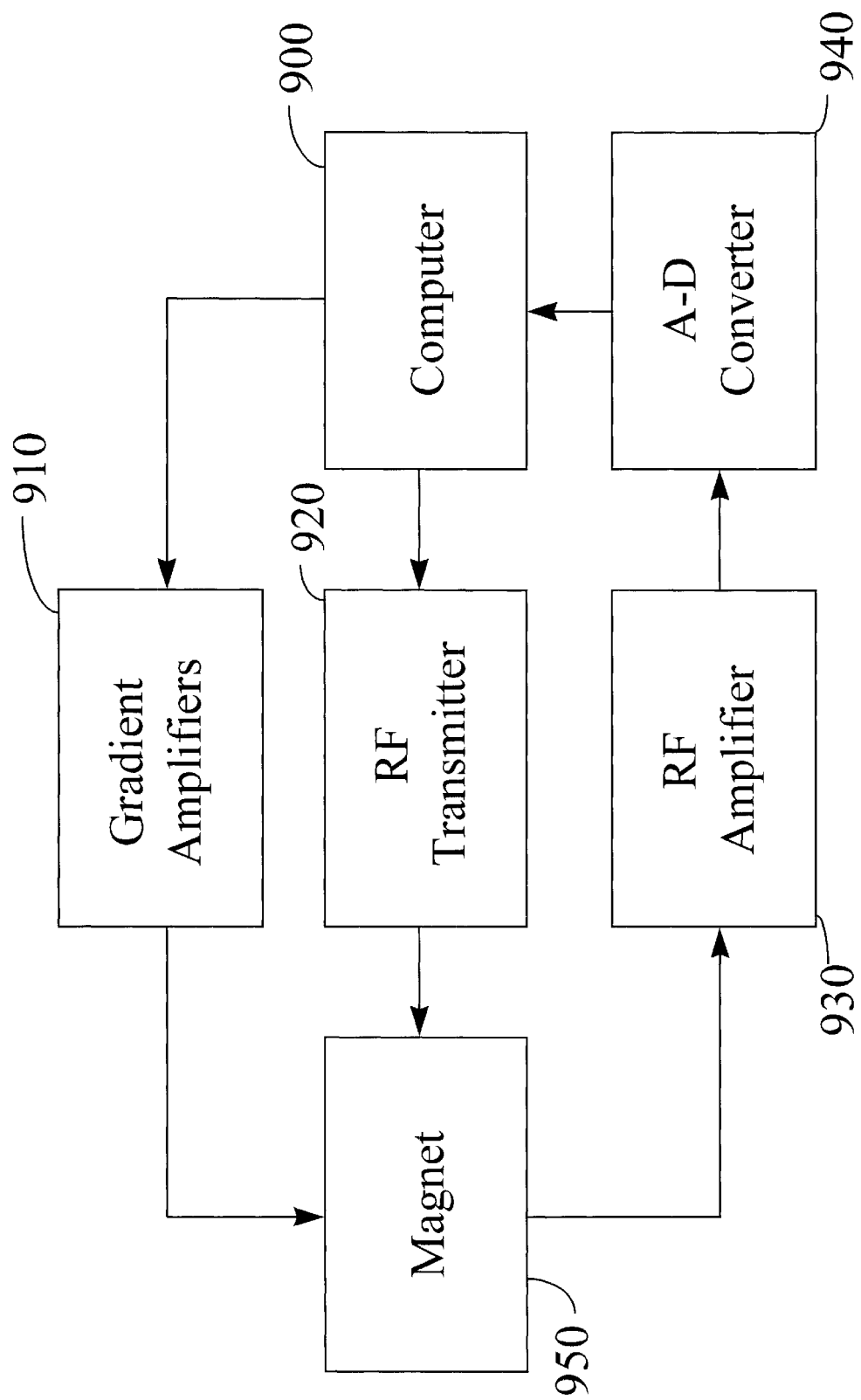
FIG. 9 is a high level block diagram of a typical MRI scanner useful in carrying out the invention.

FIG. 9 is a high level block diagram of a typical MRI scanner useful in carrying out the invention. Computer 900 directs all of the action in the MRI acquisition and acquires and processes the data. The computer tells the gradient amplifiers 910 and RF transmitter 920 when to turn on and off to obtain the proper pulse sequence. The RF receiver amplifier 930 is also controlled by the computer and relays a signal received by the RF coil from the patient to the analog to digital (A-D) converter 940 that digitizes the signal, and from there to the computer to be reconstructed into an image. Magnet 950 creates a biasing magnetic field creating alignment at an atomic level which is disturbed by the signal from the RF transmitter in a controlled manner resulting in signals sensed by RF coils feeding RF amplifier 930.

Figure 10:
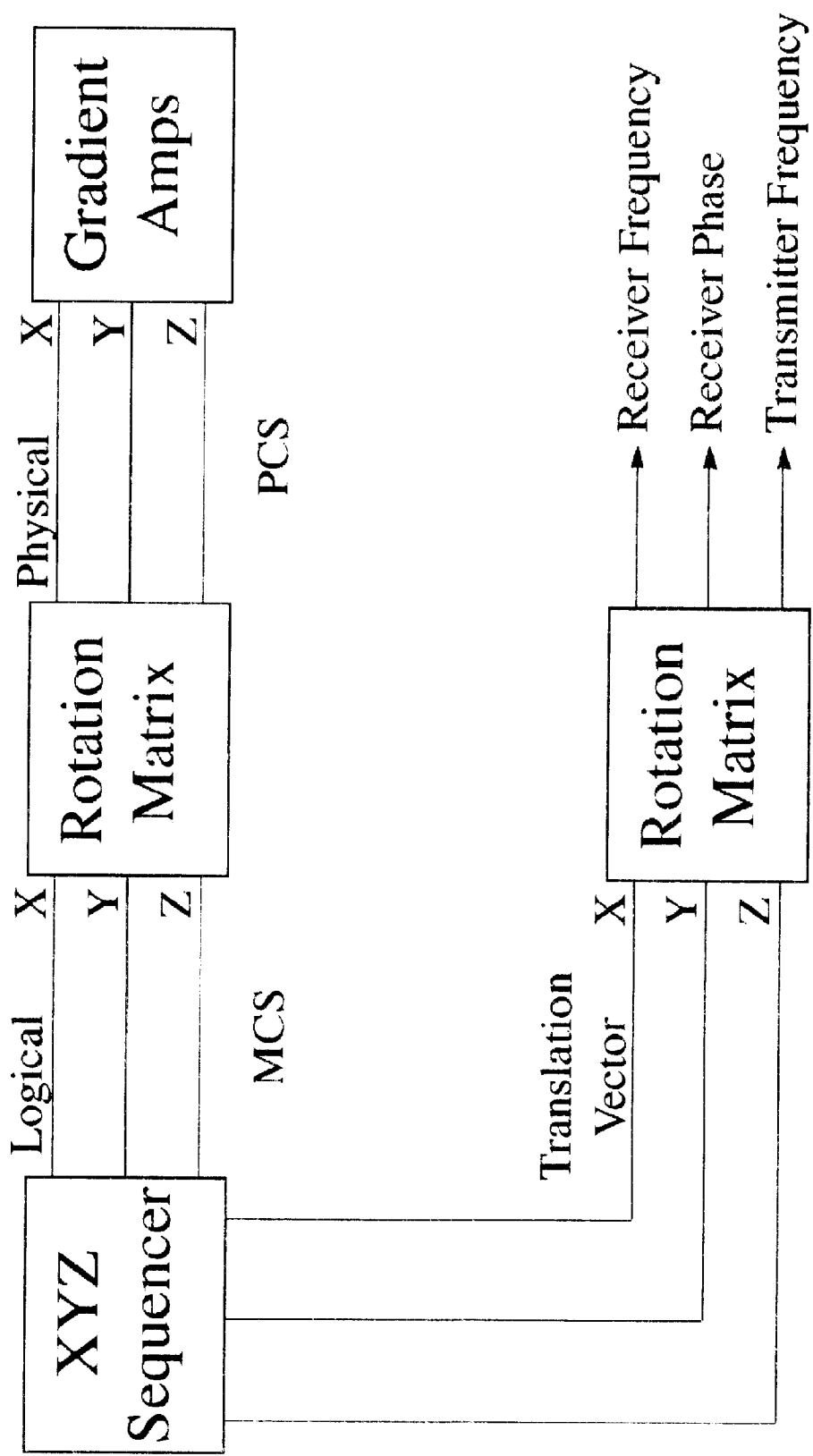
FIG. 10 is a symbolic representation of how point coordinates in a machine coordinate system are rotated and translated into a personal coordinate system.

FIG. 10 is a symbolic representation of how point coordinates in a machine coordinate system are rotated and translated into a personal coordinate system. As shown in FIG. 9, the computer 900 would normally apply logical x, logical y and logical z machine coordinate values to the gradient amplifiers to control a field at specified points in the scanning process. A coordinate system by which the machine would normally operate is transformed into a personal coordinate system (physical x, physical y, physical z) by transformation using a rotation matrix 1000. The actual signals received by gradient amplifiers 1020 are then based on the personal coordinate system rather than the machine coordinate system. This permits data to be stored with reference to the stereotactic device on the patient, rather than with reference to a particular machine. This machine independence, as discussed elsewhere in the application, permits reproduceability in the obtaining of scanned data.

Also as shown in FIG. 10, components of a translation vector are transformed by the rotation matrix to control the receiver frequency, the receiver phase and transmitter frequency, respectively.

Figure 11:
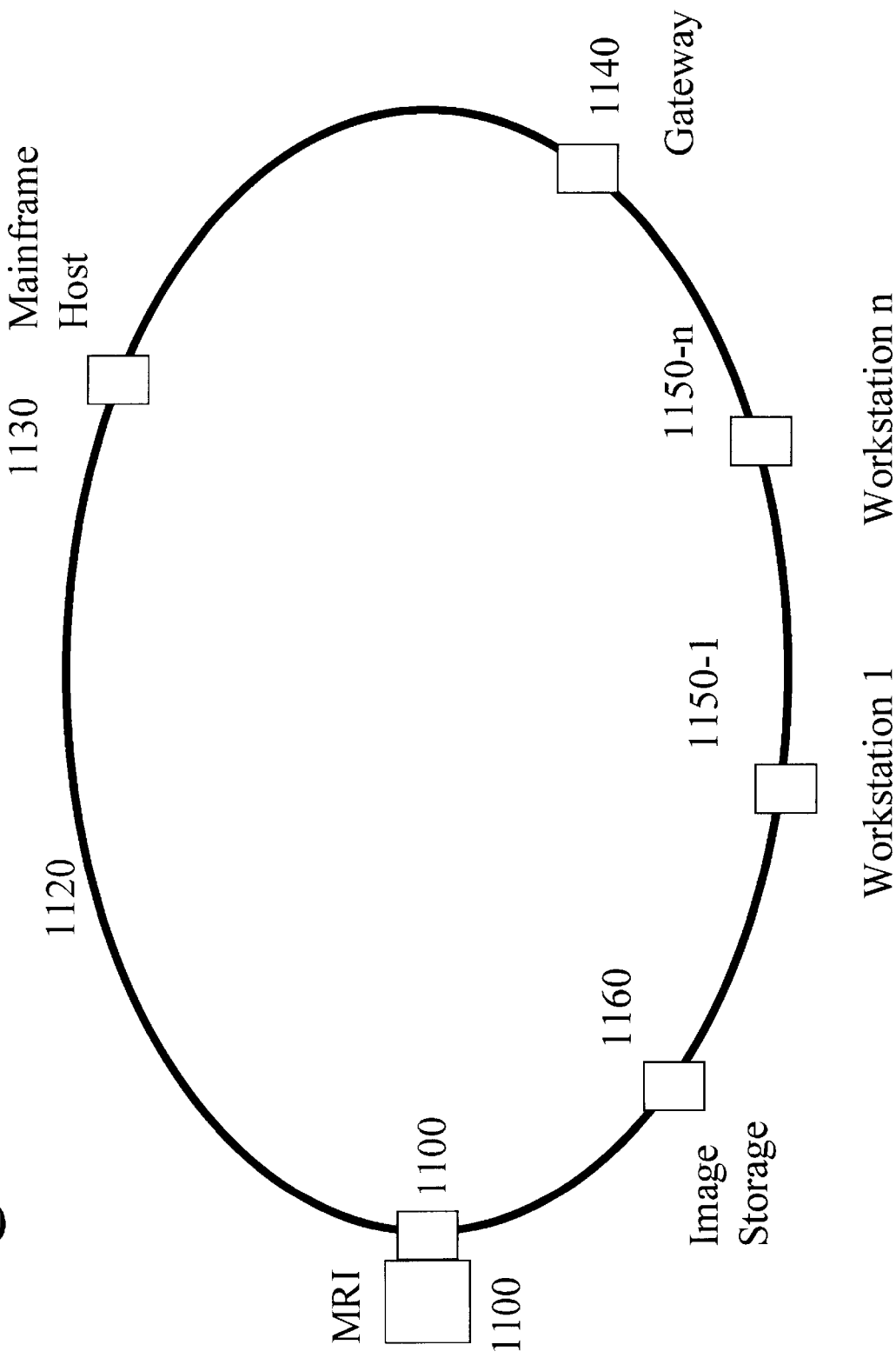
FIG. 11 is an illustration of how an MRI machine interfaces with a network.

FIG. 11 is an illustration of how an MRI machine interfaces with a network. A computer of the MRI machine 1100 has a network card 1110 which provides an interface to, for example, local area network 1120. The local area network may have a number of computers or peripheral devices attached thereto. For example, a mainframe host computer 1130 a gateway to other networks 1140 and Workstations 1-n (1150-1, 1150-n) may also be connected to the network. In addition, image storage 1160 may provide network access to images stored in electronic, optical or microphotographic formats. Such a network environment may be typically found in a hospital in which the various departments are linked over the local area network and in which doctors or other authorized personnel may wish to review stored images of MRI scans or other radiographic scanning of a patient.

Figure 12:
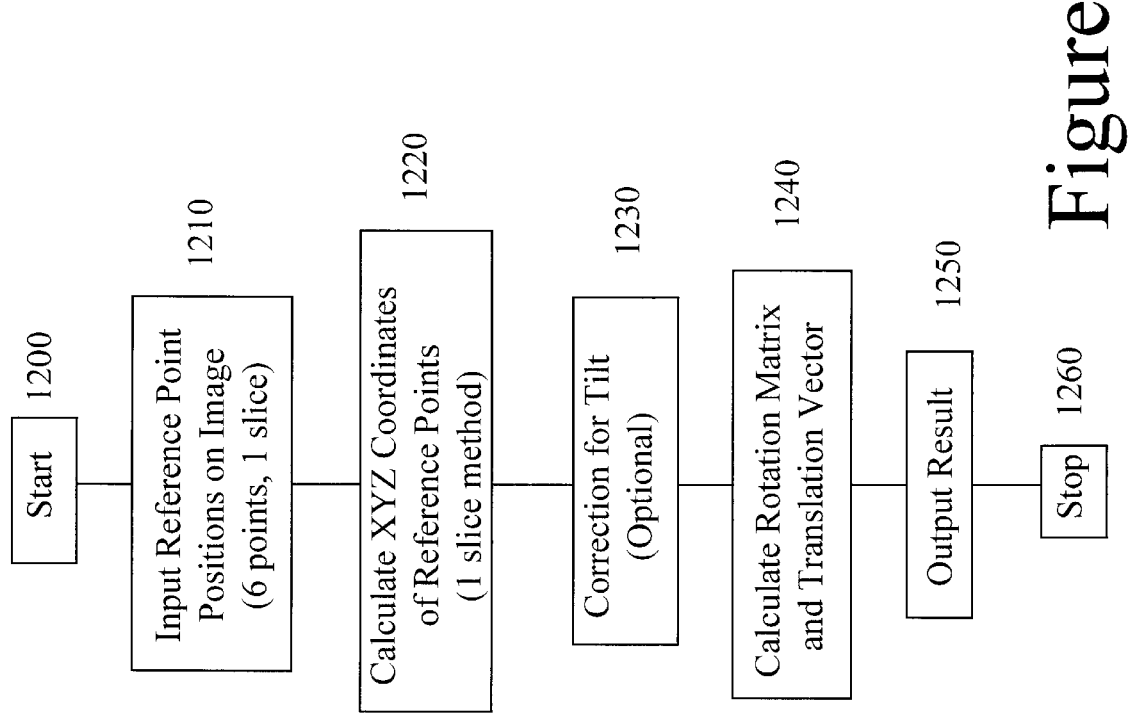
FIG. 12 is a flow chart of a single slice method of determining a rotation matrix and a translation vector.

FIG. 12 is a flow chart of a single slice method of determining a rotation matrix and a translation vector. The process begins (1200) and the reference points which represent the 6 points at to which the single slice intersects each pair of reference elements tubes as shown for example by the slice line in FIG. 3 are input or otherwise made available. These points are identified, for example, in FIG. 4a as points a, b, c, d, e and f.

With the image point positions identified on the slice, the xyz coordinates of the reference points for each set of reference element tubes are determined utilizing in the one slice method discussed above. An optional correction for tilt (1230) can be made and then a rotation matrix and translation vector (1240) are calculated and the result output for use (1250) in machine coordinate system to personal coordinate system transforms and subsequent imaging.

Figure 13:
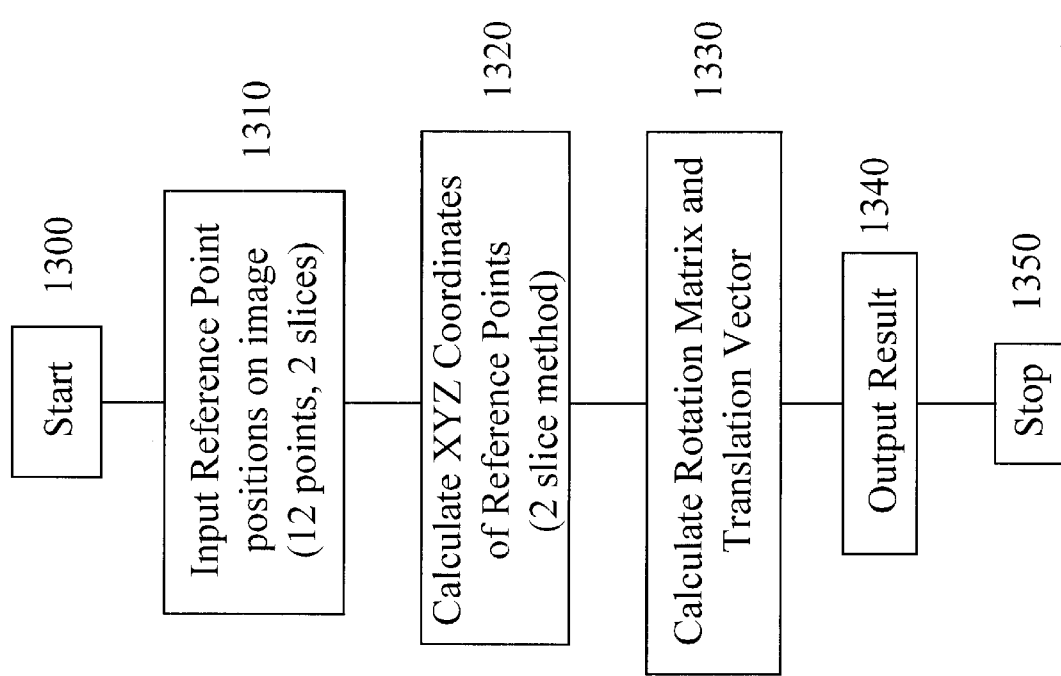
FIG. 13 is a flow chart of a 2 slice method of determining a rotation matrix and a translation vector.

FIG. 13 is a flow chart of a 2 slice method of determining a rotation matrix and a translation vector. When the process starts (1300) 12 points are input or otherwise made available corresponding to 6 points on each of 2 slices (1310). The xyz coordinates or reference points are calculated utilizing the 2 slice method (1320) discussed above and the results utilized to calculate a rotation matrix and translation vector (1330) which are then utilized (1340) in the same manner as the rotation matrix and translation vector in the single slice method (1340), and the process ends (1350).

Figure 14:
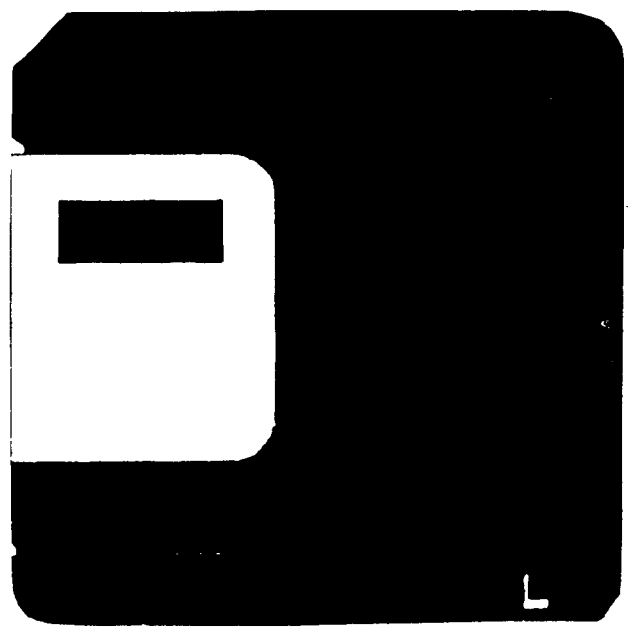
FIG. 14 is an illustration of an exemplary memory medium for storing one or more computer programs in accordance with the invention.

FIG. 14 is an illustration of an exemplary memory medium for storing one or more computer programs in accordance with the invention. In this example, memory medium 1400 is a floppy diskette which can be utilized to store program information and related data and to load it into a computer such as a computer controlling the MRI machine.

Described above are improved devices and procedures for non-invasive, radiographic analysis, particularly stereotactic head examinations, e.g., in connection with stereotaxy or other similar surgical procedures, meeting the objects of the invention. Some of the more noteworthy features of the invention include, but are not limited to:

1. A stereotactic device that can be made with extremely low cost and which can be made in disposable or re-usable form;
2. A method of aligning the imaging plane in which only one axial image through the device is necessary to perform the subsequent alignment; the only human intervention required is the identification of the reference points ("dots") of the personal coordinate system on the localizing axial image; the rest of the process can be implemented in the imagery and processed automatically; moreover, with an automated mechanism to identify the "dots," the entire process can be fully automated;
3. Imaging scans acquired according to the invention are alignable to a reproducible reference coordinate system, so that the images from different examinations can be compared directly; these examinations could be performed at different institutions, with different imagers, etc., as long as all examinations are taken with a device of the invention positioned on the subject;
4. A device and method best used in obtaining MR images; however, other imaging modalities, such as CT, PET, SPECT, or MEG, are also applicable; these other imaging modalities can then be cross-referenced with MR imaging scans.

The stereotactic device of the invention is exemplified as an eyeglass-like structure. However, the invention may be of any suitable structure that can support the localizing arrays or reference elements and which can be reproducibly positioned on the subject. Hence, the invention provides a way of mapping an anatomical region of a subject which can be related to a personal coordinate system that is independent of the machine coordinate system. Furthermore, the device and methods of the invention may also be amenable to veterinary applications.

It should thus be apparent that the present invention provides a method of obtaining imaging scans of a subject comprising the steps of: providing a subject with a non-invasive stereotactic device that is positioned reproducibly on the subject and which establishes a personal coordinate system (PCS). The PCS is associated with the subject independent of a machine coordinate system (MSC) that is associated with an imager; taking, using an imager having an MCS, an imaging scan of the subject including the stereotactic device to establish the PCS of the subject; manipulating the MCS of the imager to bring the MCS in substantial alignment with the PCS of the subject; and taking one or more additional imaging scans of the subject with the MCS of the imager substantially aligned with the PCS of the subject, to obtain a first set of imaging scans.

The method of the invention may further comprise repeating the above-mentioned steps at a second time period, using a second imager, to obtain a second set of imaging scans. Subsequently, at least one imaging scan of the first set can be compared with at least one imaging scan of the second set. In this way, an operator has the opportunity to note and make a record of any previously undetected anatomical feature of the subject. Moreover, observations can be made of any changes in any previously detected anatomical feature of the subject. As mentioned above, such anatomical features may be of anything that can be of interest to the subject or the medical practitioner, including but not limited to lesions, tumors, or features that may indicate a pathological condition. Adventitiously, the stereotactic device is positioned reproducibly on the subject's head.

The second time period of the disclosed method represents an elapsed time from the taking of the first set of imaging scans to the taking of the second set of imaging scans. This elapsed time may, of course, be any time period appropriate to the examination process, including periods that are very short (e.g., essentially back-to-back scans), intermediate (e.g., days to weeks), or very long (e.g., years). For instance, the elapsed time period may be about 15 to about 45 minutes, a few hours, one day to about one week, about one week to about one month, about one month to about six months and about six months to about one year. This second time period may even represent an elapsed time from the taking of the first set of imaging scans to the taking of the second set of imaging scans of about one year to about five years.

Separately, the invention provides a method of obtaining imaging scans of a subject comprising the steps of (a) providing a subject with a non-invasive stereotactic device that is positioned reproducibly on a subject and which establishes a personal coordinate system (PCS) associated with the subject which is independent of a machine coordinate system (MSC) associated with an imager; (b) taking, using a first imager having a first MCS, at least one imaging scan of the subject including the stereotactic device to establish the PCS of the subject and to relate the PCS of the subject to the first MCS of the first imager; (c) taking, using a second imager having a second MCS, at least one imaging scan of the subject including the stereotactic device to reestablish the PCS of the subject and to relate the PCS of the subject to the second MCS of the second imager; and (d) manipulating the second MCS, such that the PCS is related to the second MCS in substantially the same way as the PCS is related to the first MCS.

In this method of the invention, the second MCS is substantially aligned with the first MCS. In a specific embodiment, the first imager may be an imager in which the machine coordinate system cannot be adjusted to the personal coordinate system (i.e., the machine coordinate system is fixed, as with a CT scanner). If so, the second imager is one whose machine coordinate system is adjustable, preferably, an MR imager. The method involving different imaging modalities may further comprise forming a composite image including information from at least one imaging scan taken using the first imager and information from at least one imaging scan taken using the second imager.

In addition, the present invention also relates to a method of spatially aligning at least two radiographic imaging scans of the head of a subject taken by a radiographic scanning device comprising: (a) radiographically scanning the head of a subject wearing a stereotactic device of the invention to provide a first radiographic imaging scan containing a plurality of reference points defining a first personal coordinate system; (b) relating the first personal coordinate system with a personal coordinate system obtained from a prior radiographic imaging scan of the subject reproducibly wearing the stereotactic device; (c) adjusting the radiographic scanning device to align the first and prior personal coordinate systems; and (d) obtaining one or more additional radiographic imaging scans of the subject with the radiographic scanning device so adjusted.

The following additional examples are provided to further illustrate preferred aspects of the invention. Nothing in these additional examples should be construed to limit the invention in any way.

6. EXAMPLES

6.1. General Method

In a generic embodiment of the invention, a pulse sequence to rotate the imaging coordinate system is executed on a clinical MR imager (e.g., a 1.5T Signa, GE Medical Systems). The rotation matrix is determined by a conventional digital data processor (e.g., a personal computer) programmed to calculate the rotation matrix from the positions of the reference points of the frame. A listing of the relevant computer programs is attached hereto, as Appendices A and B.

Those skilled in the art will appreciate that rotation of the imaging coordinate system and determination of the rotation matrix can be implemented on the image as a single step. In that case, the necessary operation is reduced to identifying the positions of the reference points (e.g., 6 points in a specific embodiment) on the first image. Hence, the required sophistication of the technologist is greatly reduced by the inventive method.

6.2. Use of an MRI-Compatible Digitizer

In a specific embodiment of the invention, the reference points in the first scan are entered into a digital data processor by means of an MRI-compatible digitizer. In this embodiment, the technologist need only mark the position of the reference elements on the first scan and the digital data processor calculates the patient-defined personal coordinate system from the digitized entries using, e.g., the computational examples given above.

6.3. FURTHER EXAMPLES

The stereotactic device and the correction procedure, described above, are used with both phantoms and human volunteers. The standard quadrature head coil is used for taking the imaging scans.

FIGS. 4A–4B show a typical set of imaging scans, which is acquired with a volunteer. As noted above, FIG. 4A is the initial axial image taken through the device, and FIG. 4B is the image taken after the manipulation step, e.g., the rotation and translation steps, is applied. All three pairs of dots are aligned with each other, indicating the imaging plane is now cutting through the three reference points. Also, the reference points are at the pre-determined locations.

To demonstrate the reproducibility of the method, the following study is carried out: First, the device is positioned on the volunteer, and the first axial MR slice is taken. Rotation/translation correction is applied and a set of multi-slice images is taken. The volunteer is withdrawn from the magnet. The device is removed, and replaced again on the subject by a different technologist. Images are taken again in the same manner as in the first scan set.

Figure 6A:
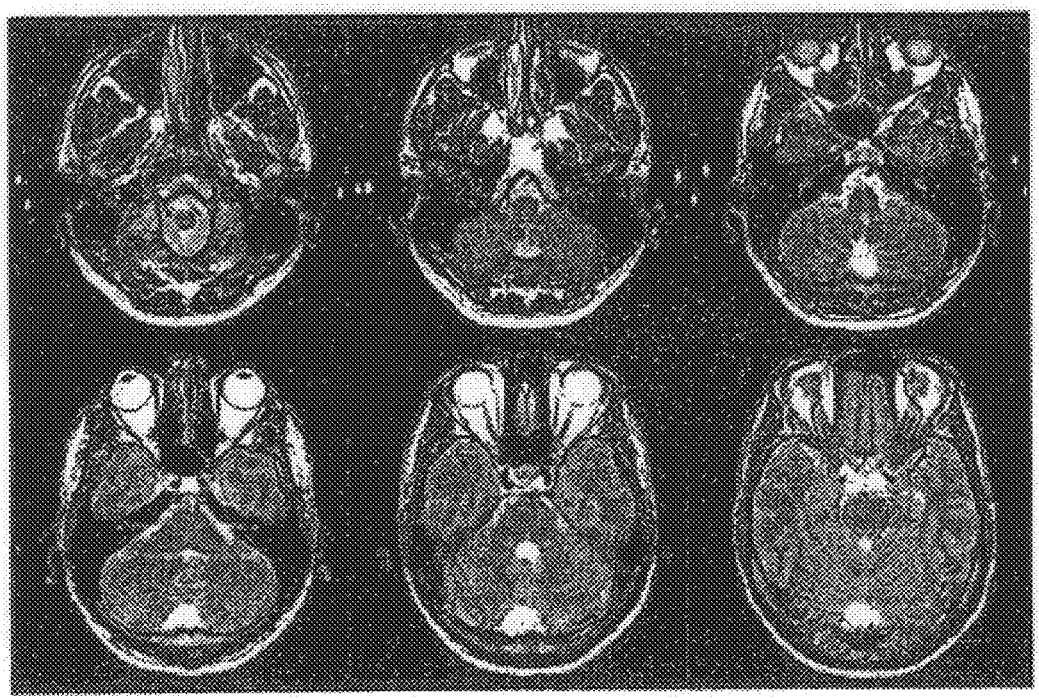
Figure 6B:
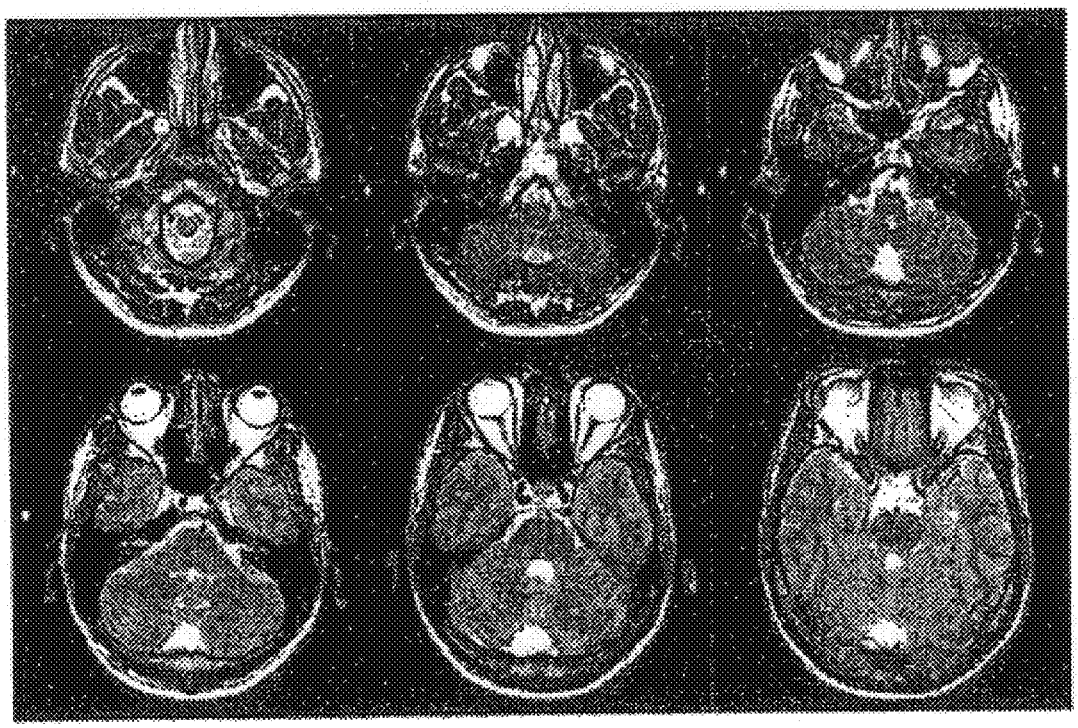
FIG. 6B depicts another scan of the same volunteer, but by a different operator, demonstrating the reproducibility of the inventive method.
Figure 7:
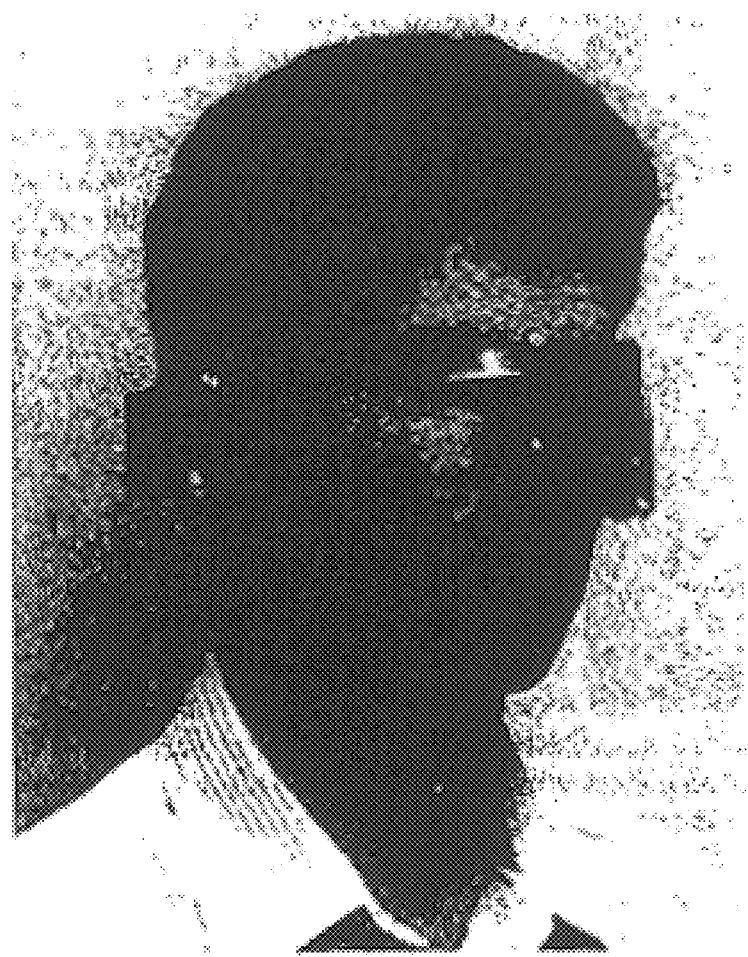
FIG. 7 depicts a volunteer wearing the device of FIGS. 1A, 1B and 1C.
Figure 8A:
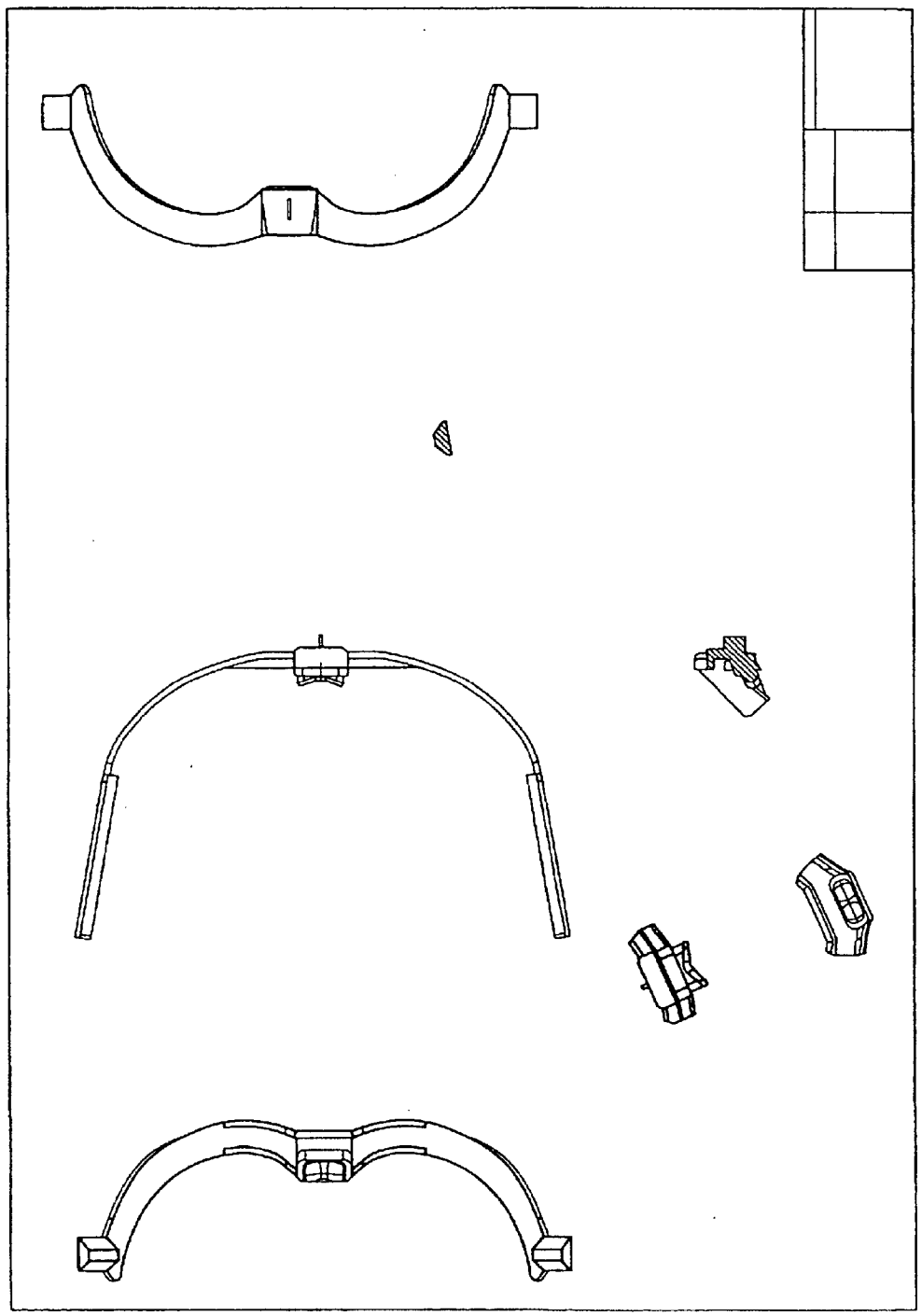
FIGS. 8A–8F depict the specifications for one embodiment of the device of the invention.
Figure 8B:
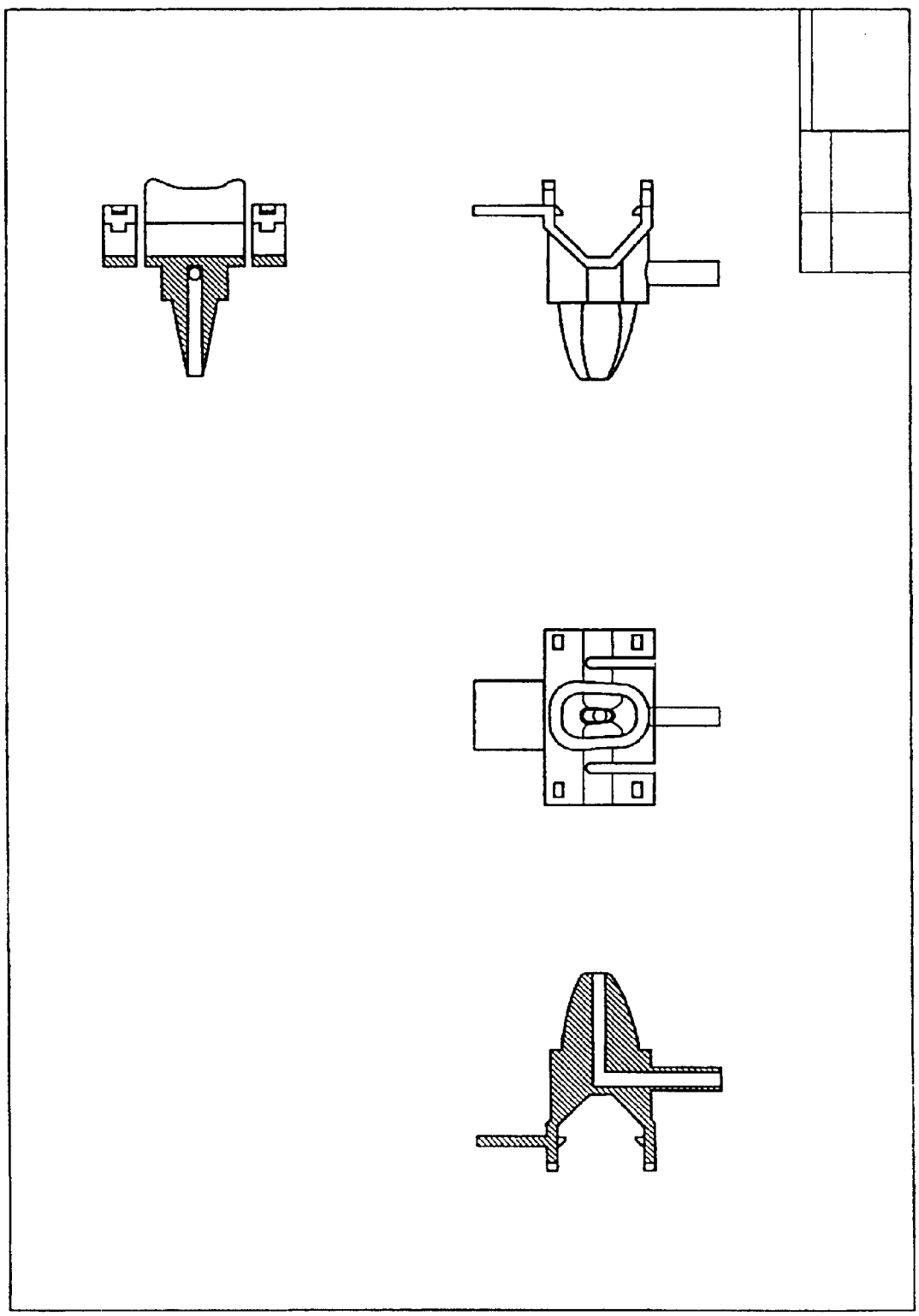
Figure 8C:
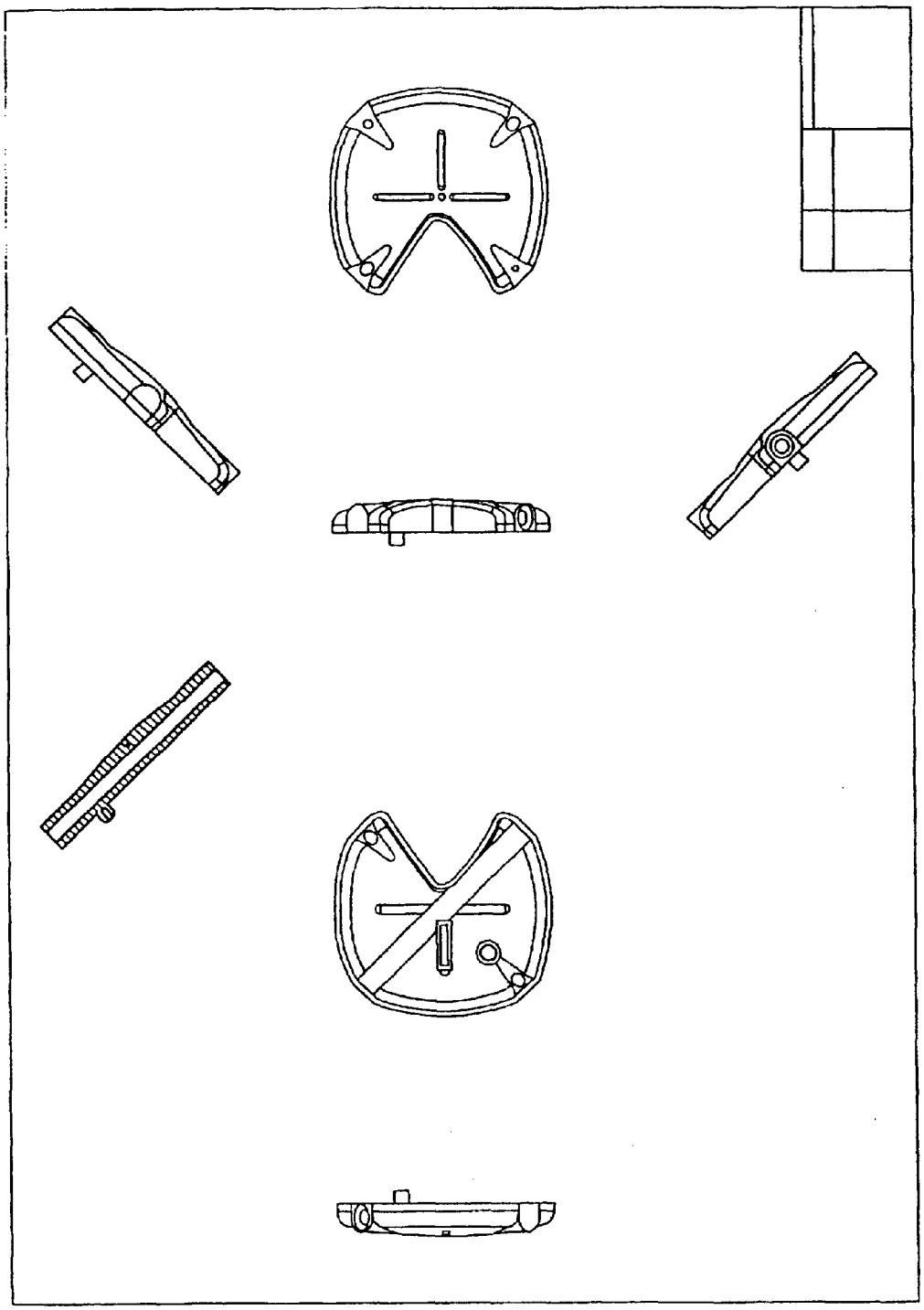
Figure 8D:
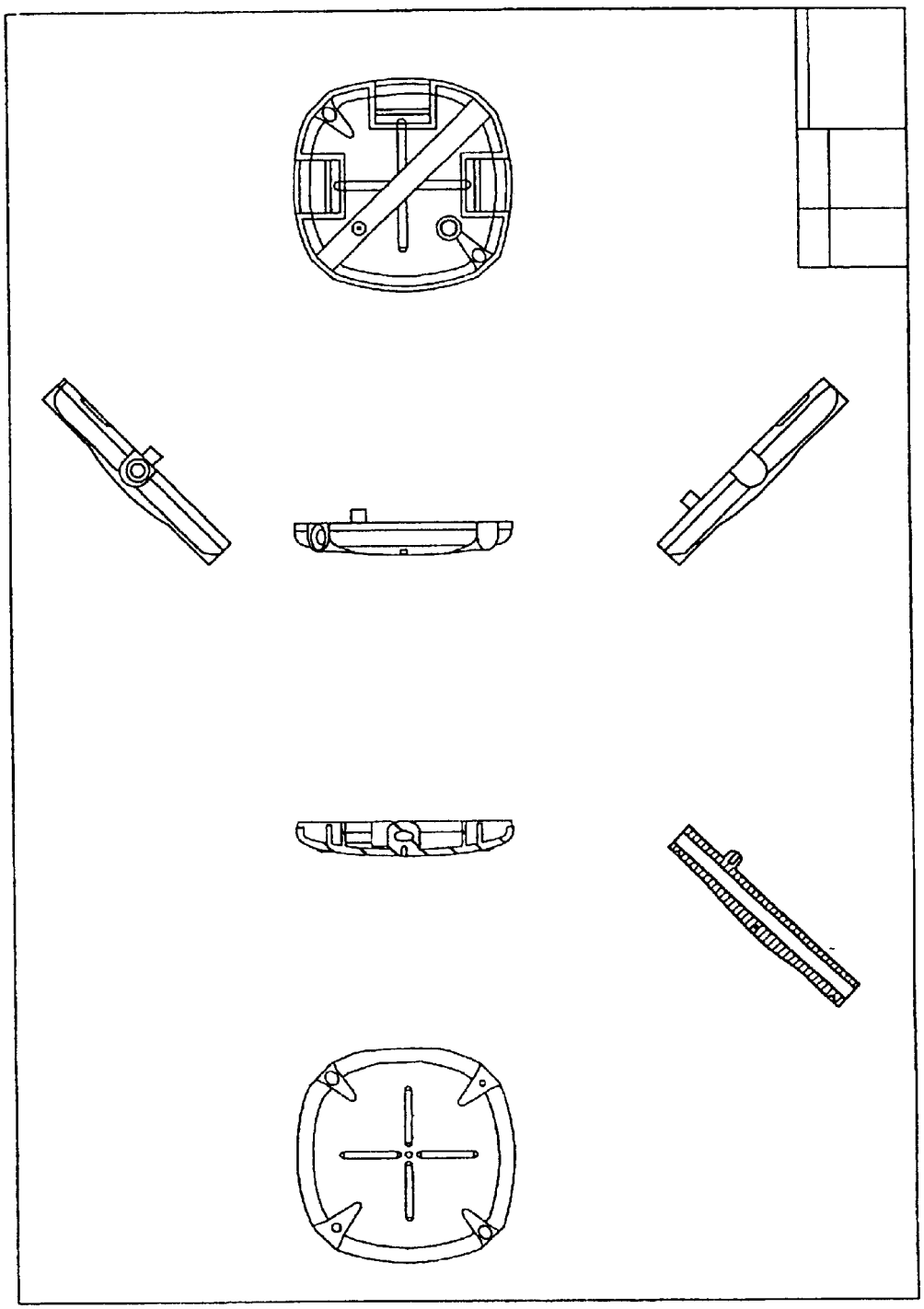
Figure 8E:
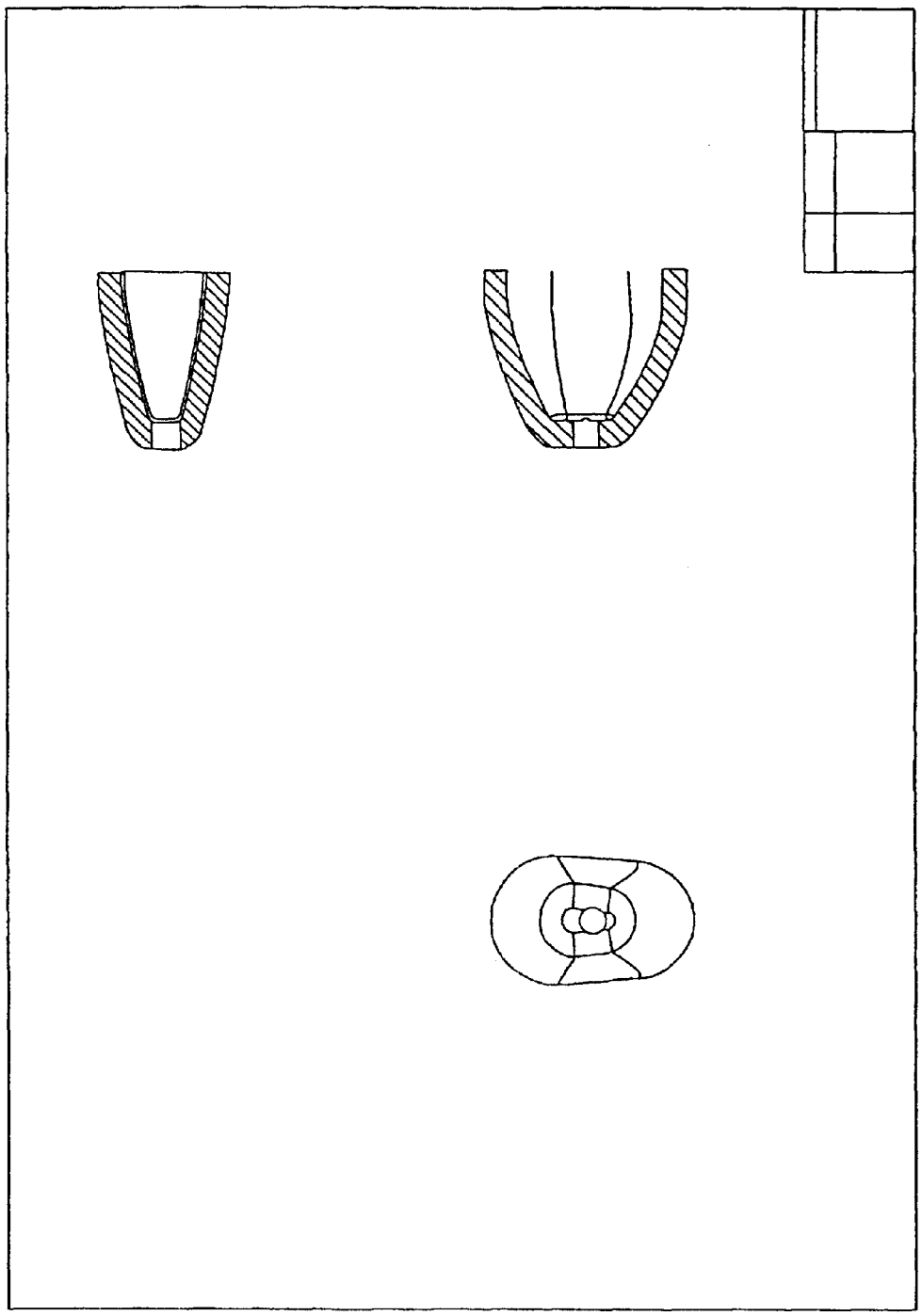
Figure 8F:
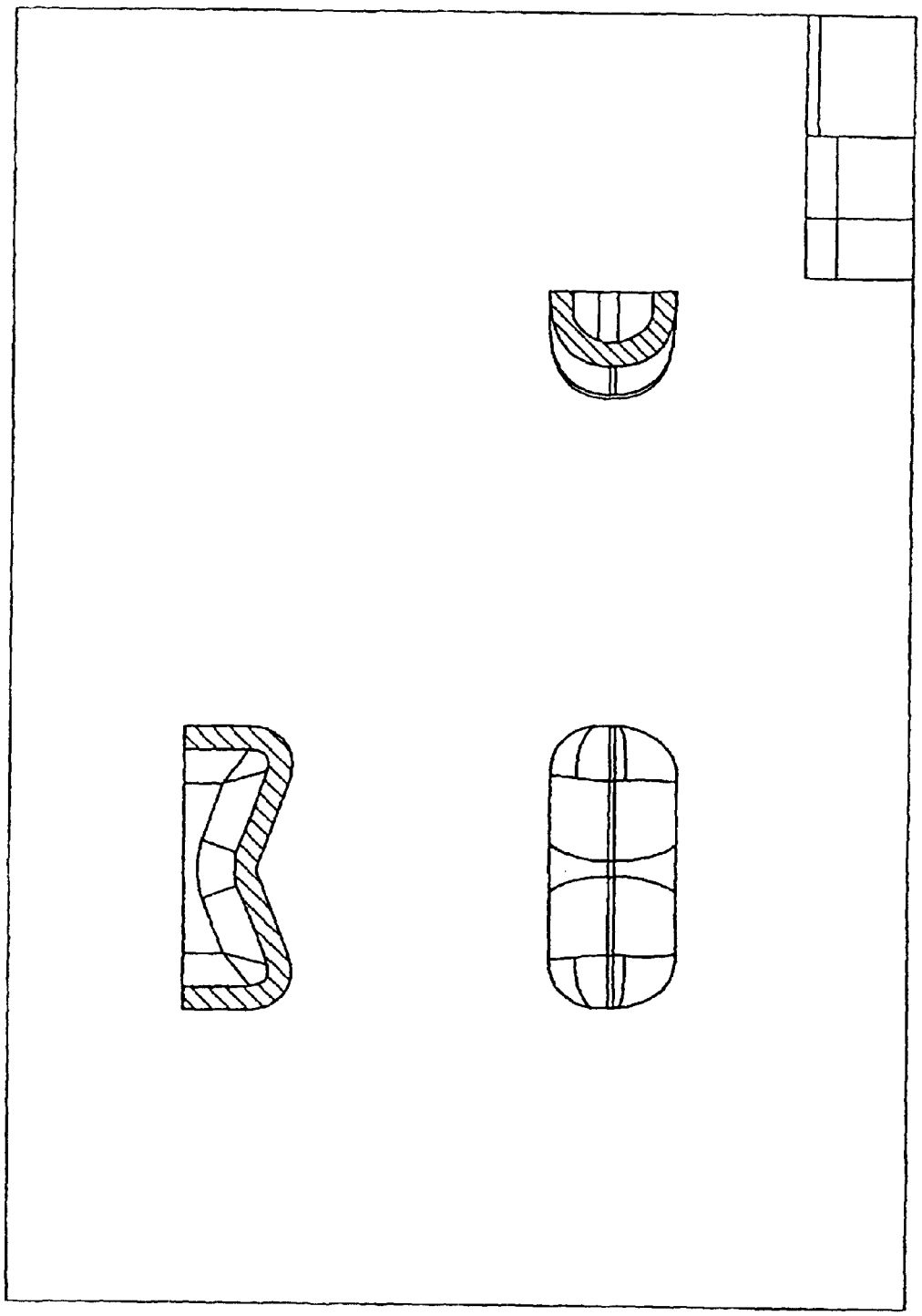

Several slices from these two examinations are shown in FIGS. 6A and 6B. FIG. 6A shows the images taken by the first operator, and FIG. 6B shows the images taken by the second operator. (Imaging parameters are: modified RARE sequence, 30 cm FOV, 256×256, 3 mm slice, single slice axial scan (FIGS. 4A and 4B) and multi-slice axial scan with 20 cm FOV (FIGS. 6A and 6B).)

As is evident from these pictures, a high degree of reproducibility in scan sections is provided by the device and method of the invention.

The accuracy in reproducing slice position and orientation between different time points is evaluated in phantom and human volunteer studies. The error in phantom studies, when using the mathematically exact, two-scan method, is about 1 mm or less! In human volunteer studies, the error is somewhat higher due to patient motion, though still readily acceptable for use in comparison of the sizes and locations of lesions from one exam to another. In particular, the device of the invention allows for routine scanning, in part because of the little time (2 to 3 minutes) required for device positioning, reference scanning and determination of reference points.

6.4. Imaging Across Different Modalities

A further aspect of the invention provides for the direct comparison of imaging scans taken with different modalities, particularly wherein at least one of the modalities has a coordinate system that is not adjustable. In this embodiment, e.g., a first scan having fixed machine coordinates is taken of the subject wearing the stereotactic device of the invention. The reference elements are located in the scan and a personal coordinate system is established therefrom. Additionally calculated is the translation and rotation of the machine coordinate system required to align the machine with the personal coordinate system.

A second scan is later taken with a modality in which the machine coordinate system can be adjusted (e.g., MR imager) with the patient reproducibly wearing the stereotactic device. The reference elements are identified in the second scan and the personal coordinate system determined. The value of the difference in the personal coordinate system and the machine coordinate systems for the initial and second scans are determined.

With the common personal coordinate system in place, the second imager is then adjusted to translate and/or rotate the second imager coordinate system so that the difference between the second image coordinate system and the second personal coordinate system coincides with the difference between the first image coordinate system and the first personal coordinate system.

Subsequent scans are then taken with the second imager aligned with the scan plane of the first imager, permitting a highly reproducible direct alignment of scans taken in the two different modalities based upon the common personal coordinate system.

The stereotactic device and procedure of the invention can thus be used to align images from modalities such as computed tomography (CT), positron emission tomography (PET), single photon emission computed tomography (SPECT), electroencephalography (EEG) or magnetoencephalography (MEG), and the like.

In the case of CT and the device of the invention, an illustrative procedure is as follows (NB: It is not possible to freely position the CT slice, hence, MR images have to be rotated to the CT plane.):

First, the CT examination is done with the device on. The position of the reference points (mid-point of the X-shaped rods) in the CT coordinate system is calculated. Next, an MR axial slice through the device is taken, and the MR coordinate system is rotated/translated to coincide with the CT coordinate system, i.e., the second machine coordinate system is substantially aligned with the first machine coordinate system. Imaging slices that are of the same location/thickness as those of the CT examination are then taken.

As is readily evident to those skilled in the art, similar procedures can be employed for aligning other imaging modalities. In this way, all imaging capabilities can be linked through the use of MR under the practice of the invention.

6.5. Follow-Up Electroencephalography (EEG)

The general positions of each electrode can be reproduced, if desired, to correspond with an initial EEG, using the device of the invention. Alternatively, each new configuration of the electrodes can be recorded digitally relative to the PCS established by the device, and MR images can be taken selectively based thereon.

When seeking a reproducible placement of electrodes for use in electroencephalography (EEG), a series of MR imaging scans is taken of a patient wearing the stereotactic device of the invention, as described above, to establish the personal coordinate system. One or more electrodes are then placed on the patient's head, and the position of the electrodes is digitized, as described above. The location of the electrodes is thereby determined and recorded relative to the personal coordinate system.

Upon subsequent EEG examinations, the patient wears the stereotactic device of the invention. One or more scans are taken to reestablish the personal coordinate system. One or more electrodes are again placed on the patient so that their positions correspond to their original positions in the initial EEG/MRI scan. Correct placement of the electrodes is checked by comparing the prior scan and electrode placement with that of the subsequent scan.

Accordingly, any changes in the electrical activity of the patient can be attributed to specific electrodes and/or patient anatomical features as revealed by the MRI.

6.6. Process for Determining Subject Head Orientation

Still another aspect of the invention provides a method for determining the orientation of a subject's head. The procedure includes placing a plurality of, preferably three, localizing arrays of the "X"-type, described above, about the head of a subject patient, e.g., substantially adjacent the nasion and ears, or in other locations spaced apart about the circumference of the head. The procedure further includes taking a cross-sectional imaging scan of the head in the vicinity of the localizing arrays and determining the orientation of the head based on the pattern of "dots" (or other distinctive features generated by the reference elements) in the imaging scan. This operation may be accomplished conveniently through use of the computer-implemented program appended hereto. Adjustments to the orientation of the subject's head can then be performed as needed or desired.

6.7. Real Time Imaging Slice Correction

It is possible to use a digitizing method that does not depend on MR imaging. For example, by putting one or more markers such as an LED for each localizing array, and calculating the LED positions using a video camera, it then become possible to get the information on the patient's head location and orientation at any time during the imaging, without waiting for the completion of the data acquisition. One application of this is to dynamically correct the imaging plane during the data acquisition, using the localizing array positions obtained through an MR independent digitizer. Thus, even if the patient's head moves during the scan, the imaging plane can be aligned to the head, and thereby compensating for the effect of the motion.

Those skilled in the art will appreciate that the embodiments described above are exemplary and that other embodiments incorporating alterations and modifications therein fall within the scope and spirit of the invention. Each of the references mentioned above is incorporated by reference herein.

What is claimed is:

1. A method of using a radiographic device comprising the steps of:
    a) positioning a living organism having a body in a radiographic device having a machine coordinate system;
    b) non-invasively positioning on said body a stereotactic device having at least three localizing arrays providing a plurality of reference elements to establish a personal coordinate system referenced to said body;
    c) establishing a linkage between said personal coordinate system and said machine coordinate system of said radiographic device;
    d) translating data captured in said machine coordinate system to data referenced to said personal coordinate system; and
    e) storing data referenced to the personal coordinate system based on a location and orientation of said stereotactic device.

2. The method of claim 1 wherein said step of establishing a linkage includes calculating a transformation matrix linking said personal coordinate system and said machine coordinate system.

3. The method of claim 1 wherein said step of establishing a linkage includes calculating a rotation matrix and a translation vector linking said personal coordinate system and said machine coordinate system.

4. The method of claim 1 wherein said step of establishing a linkage includes calculating a transformation matrix linking said personal coordinate system and said machine coordinate system using at least one slice of radiographic data.

5. The method of claim 1 wherein said step of establishing a linkage includes calculating a transformation matrix linking said personal coordinate system and said machine coordinate system using at least two slices of radiographic data.

6. A system for reproducibly capturing radiographic images, comprising:
    a) a radiographic scanner that provides output information, including position information used to control said radiographic scanner;
    b) a stereotactic device configured to be non-invasively positioned on a body of a living organism and having at least three localizing arrays providing a plurality of reference elements connected to the stereotactic device, each reference element having a location and an orientation; and
    c) a computer controlling said radiographic scanner and receiving said output information from said scanner to detect said location and orientation of said reference elements of said stereotactic device, wherein said computer is configured to store data referenced to a coordinate system defined with reference to the living organism and based on said location and orientation of said reference elements of said stereotactic device.

7. The system of claim 6 wherein said computer is configured to translate position information controlling said radiographic scanner into position information referenced to said coordinate system defined with reference to said location and orientation of said reference elements of said stereotactic device.

8. The system of claim 6, wherein the reference elements are radio opaque.

9. The system of claim 6, wherein said stereotactic device provides at least three reference elements.

10. A computer program product comprising:
    a) a memory medium; and
    b) a computer program stored on said memory medium and containing instructions for: establishing a personal coordinate system referenced to a living organism having a body, using a stereotactic device configured to be non-invasively positioned on the body and having at least three localizing arrays providing a plurality of reference elements, storing data referenced to the personal coordinate system based on a location and orientation of said stereotactic device; and establishing a linkage between said personal coordinate system and a machine coordinate system of a radiographic device.

11. The computer program product of claim 10 wherein said computer program further contains instructions for translating data captured in said machine coordinate system to data referenced in said personal coordinate system.

12. The computer program product of claim 10, wherein said instructions for determining said location and orientation of said reference elements of said sterotactic device include determining said location and orientation from at least one slice of radiographic data.

13. The computer program product of claim 10, wherein said instructions for determining said location and orientation of said reference elements of said sterotactic device include determining said location and orientation from a plurality of slices of radiographic data.

14. A method of using a radiographic device, comprising the steps of:
    a) positioning a living organism having a body in a radiographic device having a machine coordinate system;
    b) making at least one radiographic scan of said body;
    c) fitting a stereotactic device that is non-invasively positioned on the body and has at least three localizing arrays providing a plurality of reference elements connected to the stereotactic device, each reference element having a location and an orientation, to said body so that said fitting is reproducible and establishes a personal coordinate system referenced to said body;

d) using said location and orientation of said reference elements of said stereotactic device to determine said location of one or more data points referenced to said body from said at least one radiographic scan of said body; and e) storing data referenced to the personal coordinate system based on a location and orientation of said stereotactic device.

15. A method of correcting an imaging plane during data acquisition using a radiographic device and a stereotactic device configured to be non-invasively positioned on a body and having at least three localizing arrays providing a plurality of reference elements connected to the stereotactic device, each reference element having a location and an orientation, comprising the steps of capturing said location and orientation of each of a plurality of reference elements connected to a stereotactic device, using a video camera to gather image data, and using said image data from said video camera to compensate data acquired by the radiographic device for patient motion during use of said radiographic device.

16. The method of correcting an imaging plane of claim 15, where the radiographic device has at least one imaging modality selected from the group consisting of magnetic resonance imaging, magnetic resonance spectroscopy, computer-aided tomography, positron emission tomography, single photon emission computed tomography, electroencephalography, and magnetoenceophalography.

17. A method of using a radiographic device comprising the steps of:

a) positioning a living organism having a body in a radiographic device having a machine coordinate system;

b) non-invasively positioning on a nasion and in or about ears on said body a stereotactic device having three or more non-invasive fittings providing a plurality of reference elements to establish a personal coordinate system referenced to said body;

c) establishing a linkage between said personal coordinate system and said machine coordinate system of said radiographic device;

d) translating data captured in said machine coordinate system to data referenced to said personal coordinate system; and e) storing data referenced to the tersonal coordinate system based on a location and orientation of said stereotactic device.

18. The method of claim 17 wherein said step of establishing a linkage includes calculating a transformation matrix linking said personal coordinate system and said machine coordinate system.

19. The method of claim 17 wherein said step of establishing a linkage includes calculating a rotation matrix and a translation vector linking said personal coordinate system and said machine coordinate system.

20. The method of claim 17 wherein said step of establishing a linkage includes calculating a transformation matrix linking said personal coordinate system and said machine coordinate system using at least one slice of radiographic data.

21. The method of claim 17 wherein said step of establishing a linkage includes calculating a transformation matrix linking said personal coordinate system and said machine coordinate system using at least two slices of radiographic data.

22. system for reproducibly capturing radiographic images, comprising:

a) a radiographic scanner that provides output information, including position information used to control said radiographic scanner;

(b) a stereotactic device having three or more non-invasive fittings configured to be non-invasively positioned on a nasion and in or about ears on a body of a living organism and providing a plurality of reference elements connected to the stereotactic device, each reference element having a location and an orientation; and c) a computer controlling said radiographic scanner and receiving said output information from said scanner to detect said location and orientation of said reference elements of said stereotactic device, wherein said computer is configured to store data referenced to a coordinate system defined with reference to the living organism and based on said location and orientation of said reference elements of said stereotactic device.

23. The system of claim 22 wherein said computer is configured to translate position information controlling said radiographic scanner into position information referenced to said coordinate system defined with reference to said location and orientation of said reference elements of said stereotactic device.

24. The stem of claim 22, wherein the reference elements are radio opaque.

25. The system of claim 22, wherein said stereotactic device provides at least three reference elements.

26. A computer program product comprising:

a) a memory medium; and b) a computer program stored on said memory medium and containing instructions for: establishing a personal coordinate system referenced to a living organism having a body, using a stereotactic device having three or more non-invasive fittings configured to be non-invasively positioned on a nasion and in or about ears on the body and providing a plurality of reference elements, storing data referenced to the personal coordinate system based on a location and orientation of said stereotactic device; and establishing a linkage between said personal coordinate system and a machine coordinate system of a radiographic device.

27. The computer program product of claim 26 wherein said computer program further contains instructions for translating data captured in said machine coordinate system to data referenced in said personal coordinate system.

28. The computer program product of claim 26, wherein said instructions for determining said location and orientation of said reference elements of said stereotactic device include determining said location and orientation from at least one slice of radiographic data.

29. The computer program product of claim 26, wherein said instructions for determining said location and orientation of said reference elements of said stereotactic device include determining said location and orientation from a plurality of slices of radiographic data.

30. A method of using a radiographic device, comprising the steps of:

a) positioning a living organism having a body in a radiographic device;

b) making at least one radiographic scan of said body;

c) fitting a stereotactic device having three or more non-invasive fittings configured to be non-invasively positioned on a nasion and in or about ears of said body and providing a plurality of reference elements connected to the stereotactic device, each reference element having a location and an orientation, to said body so that said fitting is reproducible;

d) using said location and orientation of said reference elements of said stereotactic device to determine said location of one or more data points referenced to said body from said at least one radiographic scan of said body; and f) storing data referenced to the personal coordinate system based on said location and orientation of said reference elements.

31. A method of correcting an imaging plane during data acquisition using a radiographic device and a stereotactic device having three or more non-invasive fittings configured to be non-invasively positioned on a nasion and in or about ears of a body and providing a plurality of reference elements connected thereto, each reference element having a location and an orientation, comprising the steps of capturing said location and orientation of each of a plurality of reference elements connected to the stereotactic device, using a video camera to gather image data, and using said image data from said video camera to compensate data acquired by the radiographic device for patient motion during use of said radiographic device.

32. The method of correcting an imaging plane of claim 31, where the radiographic device has at least one imaging modality selected from the group consisting of magnetic resonance imaging, magnetic resonance spectroscopy, computer-aided tomography, positron emission tomography, single photon emission computed tomography, electroencephalography, and magnetoencephalography.

* * * * *

UNITED STATES PATENT AND TRADEMARK OFFICE
CERTIFICATE OF CORRECTION

PATENT NO. : 6,684,098 B2
DATED : January 27, 2004
INVENTOR(S) : Koichi Oshio et al.

It is certified that error appears in the above-identified patent and that said Letters Patent is hereby corrected as shown below:

<u>Column 23,</u>
Line 49, "tersonal" should read -- personal --.

Signed and Sealed this

Twenty-seventh Day of April, 2004

JON W. DUDAS
*Acting Director of the United States Patent and Trademark Office*